United States Patent
Weiss et al.

(10) Patent No.: US 6,572,488 B1
(45) Date of Patent: Jun. 3, 2003

(54) METHOD AND APPARATUS FOR LOCATING AND ALIGNING GOLF CLUB SHAFT SPINE

(75) Inventors: Richard M. Weiss, 9050 SW. 69th Ct., Miami, FL (US) 33156; Joseph H. Butler, Knoxville, TN (US); Michael J. Twigg, Memphis, TN (US)

(73) Assignee: Richard M. Weiss, Miami, FL (US)

( * ) Notice: Subject to any disclaimer, the term of this patent is extended or adjusted under 35 U.S.C. 154(b) by 0 days.

(21) Appl. No.: 09/494,525

(22) Filed: Feb. 1, 2000

Related U.S. Application Data

(60) Provisional application No. 60/135,012, filed on May 20, 1999.

(51) Int. Cl.[7] .................. A63B 53/10; A63B 53/12; G01L 1/10; G01L 1/04
(52) U.S. Cl. .............. 473/289; 73/862.59; 73/862.451; 473/409
(58) Field of Search .................. 473/289, 316–323, 473/409; 73/862.03, 862.391, 41, 42, 451, 474, 59, 61, 635, 642, 854, 1.82, 862.59, 862.642; 29/720, 407.01

(56) References Cited

U.S. PATENT DOCUMENTS

| | | | |
|---|---|---|---|
| 1,953,916 A | 4/1934 | Adams | 265/49 |
| 3,992,933 A | 11/1976 | Randolph, Jr. | 73/141 A |
| 4,122,593 A | 10/1978 | Braly | 29/407 |
| 4,169,595 A | 10/1979 | Kaugars | |
| 4,517,843 A | 5/1985 | Leger | 73/847 |
| 4,558,863 A | 12/1985 | Haas et al. | 273/77 A |
| 4,682,504 A | 7/1987 | Kobayashi | 73/854 |
| 4,958,834 A | 9/1990 | Colbert | |
| 5,040,279 A | 8/1991 | Braly | |
| 5,379,641 A | 1/1995 | Paasivaara et al. | 73/579 |
| 5,429,008 A | 7/1995 | Matsumoto et al. | 73/862.639 |
| 5,478,073 A | * 12/1995 | Hackman | |
| 5,515,717 A | 5/1996 | White | 73/65.03 |
| 5,520,052 A | 5/1996 | Pechersky | 73/579 |
| 5,771,552 A | 6/1998 | Karner et al. | |
| 5,870,815 A | 2/1999 | Karner et al. | 29/407.1 |
| 5,976,028 A | * 11/1999 | Ciccarello | |
| 6,183,375 B1 | 2/2001 | Weiss | 473/289 |
| 6,250,168 B1 | 6/2001 | D'Aguanno | |
| 6,357,285 B1 | * 3/2002 | Allen | |
| 6,415,502 B1 | 7/2002 | Gunshinan et al. | 29/714 |
| 2001/0027137 A1 | 10/2001 | Weiss | 473/289 |

FOREIGN PATENT DOCUMENTS

DE 4106572 9/1992

* cited by examiner

*Primary Examiner*—Stephen Blau
(74) *Attorney, Agent, or Firm*—Fish & Neave; Jeffrey H. Ingerman

(57) ABSTRACT

The preferred orientation, or planar oscillation plane, of a golf club shaft is located by measuring the oscillation of the shaft when a horizontal impulse is applied and from those measurements determining an orientation in which the oscillation would be substantially planar. In a preferred embodiment an iterative process is used to converge on the preferred orientation. The location of the preferred orientation may be marked on the shaft and used to assemble a golf club with the planar oscillation plane in a predetermined orientation. The assembly of the golf club can be done manually—e.g., in a refitting situation—or automatically—e.g., in a new club manufacturing setting.

26 Claims, 18 Drawing Sheets

METHOD AND APPARATUS FOR LOCATING AND ALIGNING GOLF CLUB SHAFT SPINE

CROSS REFERENCE TO RELATED APPLICATION

This claims the benefit of U.S. Provisional Patent Application No. 60/135,012, filed May 20, 1999.

BACKGROUND OF THE INVENTION

This invention relates to locating and aligning the spine of a golf club shaft. More particularly, this invention relates to a method and apparatus for automatically and reliably identifying the location of the spine of a golf club shaft and for aligning the spine in a desired orientation.

When a golfer swings a golf club, the shaft of the golf club bends or twists, especially during the downswing. The direction the shaft bends or twists is dependent on how the golfer loads or accelerates the club, but the bending or twisting direction and magnitude also are dependent on the stiffness of the shaft. If a shaft is soft, it will bend or twist more during a given downswing than if it is stiff. Additionally if a shaft exhibits different transverse stiffness in different planes—i.e., the stiffness, roundness and straightness of the shaft are not symmetric—the shaft will bend or twist differently depending upon in which plane (direction) it is loaded.

Immediately prior to the impact of the head of a golf club with a golf ball, the shaft of the golf club goes through significant vibratory movements in both the toe up/down direction (plane perpendicular to the hit direction) and in the lead/lag direction (plane parallel to the hit direction). Research has shown the shaft of a golf club vibrates up and down in the toe up/down direction immediately prior to impact with the golf ball. This up and down movement, known as "vertical deflection" or "droop," can be as large as ±1.5 inch (±3.8 cm). Because any inconsistent bending or twisting due to asymmetric shaft behavior immediately prior to impact is substantially impossible for the golfer to correct with his or her swing, any reduction in vertical deflection or droop immediately prior to impact will help the golfer improve his or her impact repeatability. This is true for golfers of all skill levels. Inconsistent bending or twisting makes it more difficult for the golfer to reproduce the downswing shaft bending or twisting from club to club, thereby resulting in less consistent impact repeatability within the set.

In addition, a golf club, immediately prior to impact, "springs" forward in the direction of the shot. This is commonly referred to as the "kick" of the shaft. If it is possible to analyze and orient a shaft in a way so that the kick direction of vibration is stable, this shaft position would improve the golfer's ability to repeat the impact position with the ball. In other words the shaft would have less of a tendency to "bob" up and down immediately prior to impact thereby improving impact repeatability.

Inconsistent bending or twisting contributes to movements of the club head that would not be present if the shaft had been perfectly symmetric. Golf club manufacturers attempt to build shafts with symmetric stiffness to minimize inconsistent bending or twisting during the swing, but as a result of manufacturing limitations it is difficult to build a perfectly symmetric golf club shaft. Specifically, it is well known that, as a result of irregularities or variations in materials or manufacturing processes, golf club shafts have a preferred angular orientation or "spine." (See, e.g., U.S. Pat. Nos. 4,958,834 and 5,040,279, which are hereby incorporated by reference in their entireties.) Therefore, substantially all golf club shafts exhibit some degree of asymmetry which results in some degree of inconsistent bending or twisting during the swing.

The asymmetric stiffness of golf club shafts can result from nonsymmetrical cross sections (shafts whose cross sections are not round or whose wall thicknesss are not uniform), shafts that are not straight, or shafts whose material properties vary around the circumference of the shaft cross section. Because it is substantially impossible to build a perfectly symmetric golf club shaft and the objective is to minimize inconsistencies from club to club in a golf club set and from set to set within a brand, it makes sense, if possible, to analyze each golf club shaft in a set of golf clubs to understand its asymmetric bending or twisting behavior and construct the golf clubs in the set to maximize consistency from club to club within a set and from set to set within a brand.

It has been recognized—e.g., in above-incorporated U.S. Pat. No. 5,040,279—that although substantially all golf club shafts exhibit some degree of asymmetry, substantially every golf club shaft exhibits at least one orientation in which, when the shaft is clamped at its proximal, or handle, end and displaced at the tip, the resultant vibration of the shaft will remain substantially planar. That is, the shaft will remain substantially in a single plane and the tip of the shaft will vibrate back and forth substantially along a line.

It is also recognized in above-incorporated U.S. Pat. No. 4,958,834 that the construction of all golf clubs within a set with their respective planar oscillation planes ("POPs") oriented in the same angular direction relative to their respective club faces will exhibit less inconsistency in shaft bending or twisting during the downswing than a set that has been haphazardly or randomly constructed. In particular, a set of golf clubs normally will function best if the respective preferred angular orientations of the respective golf club shafts are aligned in the "hit direction"—i.e., substantially perpendicularly to the respective golf club faces.

However, heretofore there has not been any convenient automated way to determine the preferred angular orientation of a golf club shaft. It would be desirable to be able to provide a method and apparatus for quickly and reliably determining the preferred angular orientation of a golf club shaft. It also would be desirable to be able to provide a method and apparatus for using the determination of the preferred angular orientation to automatically assemble golf clubs with each respective golf club shaft consistently aligned relative to the respective club face.

SUMMARY OF THE INVENTION

It is an object of this invention to attempt to provide a method and apparatus for quickly and reliably determining the preferred angular orientation of a golf club shaft.

It is also an object of this invention to attempt to provide a method and apparatus for using the determination of the preferred angular orientation—e.g., the planar oscillation plane—to automatically assemble golf clubs with each respective golf club shaft consistently aligned relative to the respective club face.

In accordance with the present invention, there is provided a method of determining a preferred angular orientation of a golf club shaft about a longitudinal axis thereof, where the golf club shaft has a proximal end for gripping by a golfer and a distal end for attachment to a golf club head. According to the method, the proximal end of said golf club shaft is immobilized, and vibratory motion of the distal end of the golf club shaft is initiated in a direction other than parallel to the longitudinal axis. The vibratory motion is analyzed, and from the analyzed vibratory motion the preferred angular orientation is calculated. The golf club shaft can then be marked to indicate the preferred angular orientation. In a further method according to the invention, the mark on the shaft indicating the preferred angular orientation can be used to automatically assemble a golf club with the golf club shaft in a predetermined alignment relative to the face of the golf club head.

Apparatus for determining the preferred angular orientation, and for assembling golf clubs, are also provided.

BRIEF DESCRIPTION OF THE DRAWINGS

The above and other objects and advantages of the invention will be apparent upon consideration of the following detailed description, taken in conjunction with the accompanying drawings, in which like reference characters refer to like parts throughout, and in which.

DETAILED DESCRIPTION OF THE INVENTION

Figure 1:
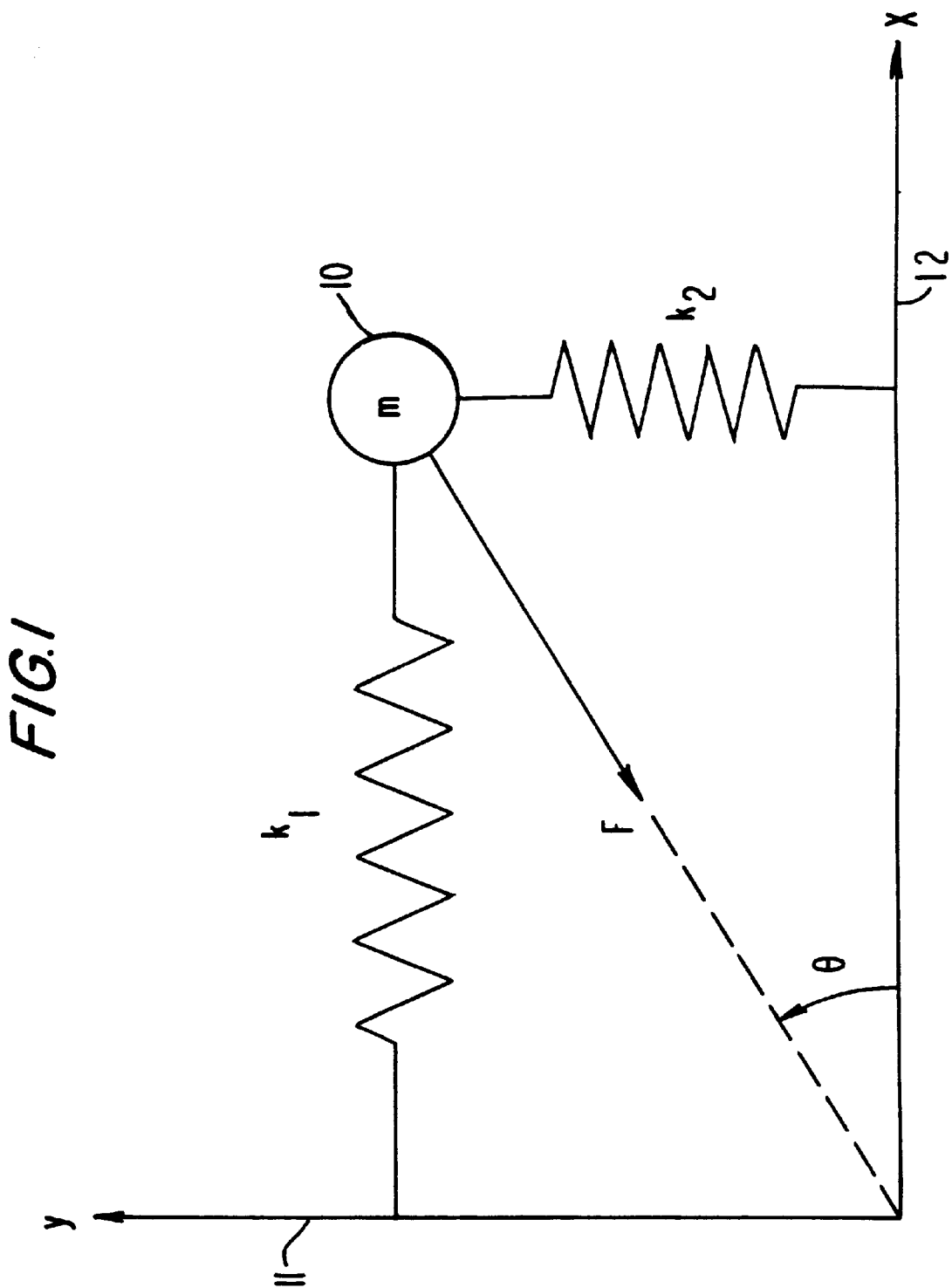
FIG. 1 is a diagram in which a flexible golf shaft is modeled as a shaft to which springs are attached.

If a golf club shaft is immobilized at its handle end and displaced in a direction perpendicular to its longitudinal axis, then if the displacement direction lies in the planar oscillation plane of the shaft, the shaft will vibrate in that plane and, viewed end on, the distal tip of the shaft will oscillate back and forth along a line. For convenience, that line can be referred to as the x-axis. However, if the displacement direction is in a plane other than the planar oscillation plane, the distal tip of the shaft will vibrate in a motion having components along the x-axis as well as along an axis perpendicular to the x-axis, which for convenience can be referred to as the y-axis. This motion could be described as an orbital, motion, although rather than tracing a single ellipse or other closed curve, the tip will move within an envelope such that, if the motion would not damp out (as it in reality does), the tip eventually would move through every point within that envelope.

As described below, by observing the tip vibration of the shaft, one can calculate mathematically the orientation of the planar oscillation plane or planes. Having located the planar oscillation plane, one can then assemble a golf club, orienting the shaft relative to the golf club head so that the planar oscillation plane is lined up along the "hit direction"—i.e., substantially perpendicular to the hitting face of the club head. It is also possible, having located the planar oscillation plane of a golf club shaft, to align the planar oscillation plane relative to the golf club head not along the hit direction, but in another predetermined direction. For example, it may be desirable to align the shaft for a particular golfer to correct or induce a hook or a slice.

It has been observed empirically that a golf club shaft is stiffer in one direction along any planar oscillation plane than it is in the opposite direction along that planar oscillation plane. This corresponds to a stiffer side of the planar oscillation plane of the shaft, which can be referred to as the "hard" or "forward" side of the planar oscillation plane, while the less stiff side, 180° opposite the hard side, can be referred to as the "soft" or "rear" side of the planar oscillation plane. It has further been observed that while orienting the planar oscillation plane perpendicular to the club head face brings a clear and dramatic improvement over a haphazard or random alignment, aligning the planar oscillation plane perpendicular to the club head face with the hard side of the planar oscillation plane facing toward the club head face brings an even further improvement, as compared to aligning the planar oscillation plane perpendicular to the club head face with the soft side of the planar oscillation plane facing toward the club head face. Moreover, if every golf club in a set of golf clubs is similarly aligned, there is a greater likelihood that the user of those clubs will be able to achieve more uniform and consistent results across all golf clubs in the set, which can be expected to result in performance enhancement.

In addition, it has been observed empirically that a golf club shaft may have several planar oscillation planes. However, it has been found that there is a principal planar oscillation plane ("PPOP"), which also may be referred to as the plane of uniform repeatability ("PURE"), that corresponds to the "spine" of the golf club shaft. Golf clubs aligned based on the principal planar oscillation plane can be expected to result in optimal performance enhancement.

The preferred direction of the planar oscillation plane—i.e., in the case of the principal planar oscillation plane, the "hard" side of the spine of the golf club shaft—cannot be determined mathematically from mere observation of the shaft tip. Therefore, in a preferred embodiment of the invention, the handle end of the golf club shaft is immobilized, the tip of the shaft is displaced perpendicular to the longitudinal axis, and the restoring force—i.e., the force tending to move the tip back to its neutral position—is measured while the shaft is rotated, from the handle end, through at least about 360°. The angle at which the restoring force is greatest is an indication of the hard side of the spine of the shaft. Although this angle usually will not align precisely with the orientation of the principal planar oscillation plane, it will indicate which of the two possible orientations of the principal planar oscillation plane corresponds to the hard side of the principal planar oscillation plane. Moreover, starting one's analysis at the angle of maximum load can be expected to lead one to find the principal planar oscillation plane rather than one of the other planar oscillation planes of the shaft.

Although it is possible to derive the orientation of the planar oscillation plane precisely using mathematical techniques based on data collected by displacing the shaft tip and allowing the shaft to vibrate, it is computationally simpler to derive the orientation by an iterative technique as described below. In such a technique, the starting orientation can be selected arbitrarily, but preferably the starting orientation is the angle of maximum restoring force, determined as described above, to maximize the likelihood that the planar oscillation plane that is found is the principal planar oscillation plane.

Once the preferred angular orientation of the golf club shaft has been determined, a mark preferably is made on the shaft to indicate the preferred angular orientation. The mark may be made at the location of the planar oscillation plane, or at a predetermined relative position with respect to the planar oscillation plane. This mark can be made using ink or paint, or can be etched into the surface of the shaft using mechanical, electrostatic or laser marking techniques. Once the mark has been made, it can be used to align the shaft relative to a golf club head when assembling a golf club, so that the spine of the golf club shaft is substantially perpendicular to, or at some other desired orientation with respect to, the club head face.

The alignment of the shaft to the club head can be performed manually. Preferably, alignment is facilitated by providing a marking on the club head as well, near the hosel, to which the marking on the shaft can be aligned to form a properly "spine-aligned" golf club. Alternatively, in another preferred embodiment, an assembly machine mates a golf club head to a golf club shaft, matching up the alignment markings in the process. In this embodiment, the golf club head can be attached to the shaft immediately after determination of the preferred angular orientation of the shaft, with the shaft still in the chuck of the spine locating station (in that case, the application of a visible mark to the shaft exterior can be omitted, although it would still be useful for later repair operations when the club is disassembled). Alternatively, in a second variant of this embodiment, the shaft can be removed from the spine locating station and moved to a club assembly station. This variant better accounts for any speed differential between the spine locating process and the club assembly process. If the spine locating process is faster than the club assembly process, more club assembly stations than spine locating stations can be provided. If the club assembly process is faster than the spine locating process, more spine locating stations than club assembly stations can be provided. In either case, it is preferable to provide a hopper or other intermediate station for holding spine-aligned shafts between the spine locating station and the club assembly station. Normally, one would expect few shafts to be held in the hopper, but if for some reason there is a breakdown or other bottleneck at or downstream of the club assembly station or stations, the hopper can serve, until it is full, as a reservoir to accept shafts from the spine locating station or stations.

The invention will now be described with reference to FIGS. 1–19.

If the handle end of a golf club shaft is clamped in a clamp that holds the shaft horizontally, then looking toward the tip of the distal end of the shaft, the shaft stiffness can be modeled, as shown in FIG. 1. As seen in FIG. 1, shaft 10 can be considered as a mass m having two springs of different spring constants $k_1$ and $k_2$ connecting it in two orthogonal directions to two different surfaces 11, 12. If shaft 10 were symmetrically stiff, then $k_1$ and $k_2$ would be equal. Normally, however, $k_1$ and $k_2$ are different. In fact, if one were to clamp the shaft in several different orientations, and each time measure the horizontal and vertical restoring forces, one might get different sets of values for $k_1$ and $k_2$. The force F, as shown, is the force imposed to displace the tip of clamped shaft 10, e.g., to cause the tip to oscillate.

Figure 2:
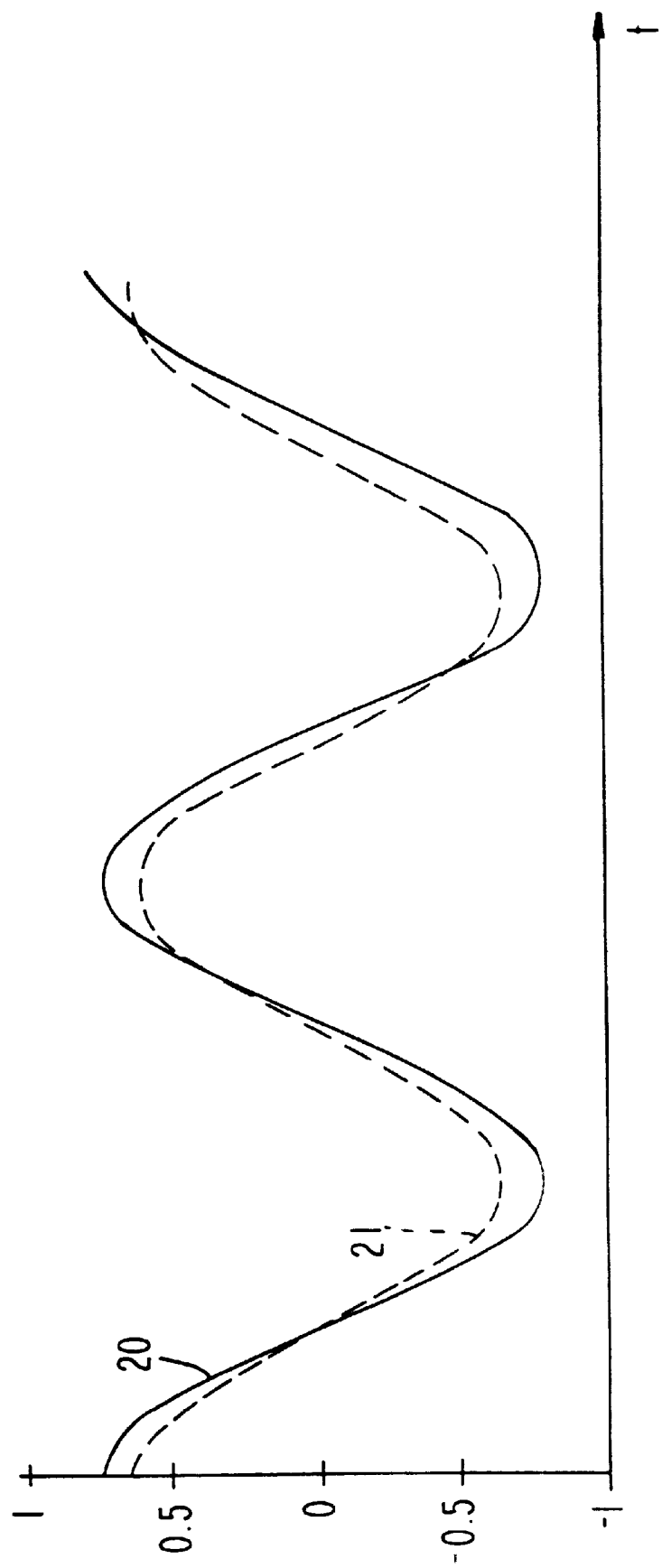
FIG. 2 shows the horizontal and vertical displacement, seen end-on, of the shaft of FIG. 1 as a function of time, over two oscillation cycles after an impulse is delivered to cause the shaft to oscillate.
Figure 3:
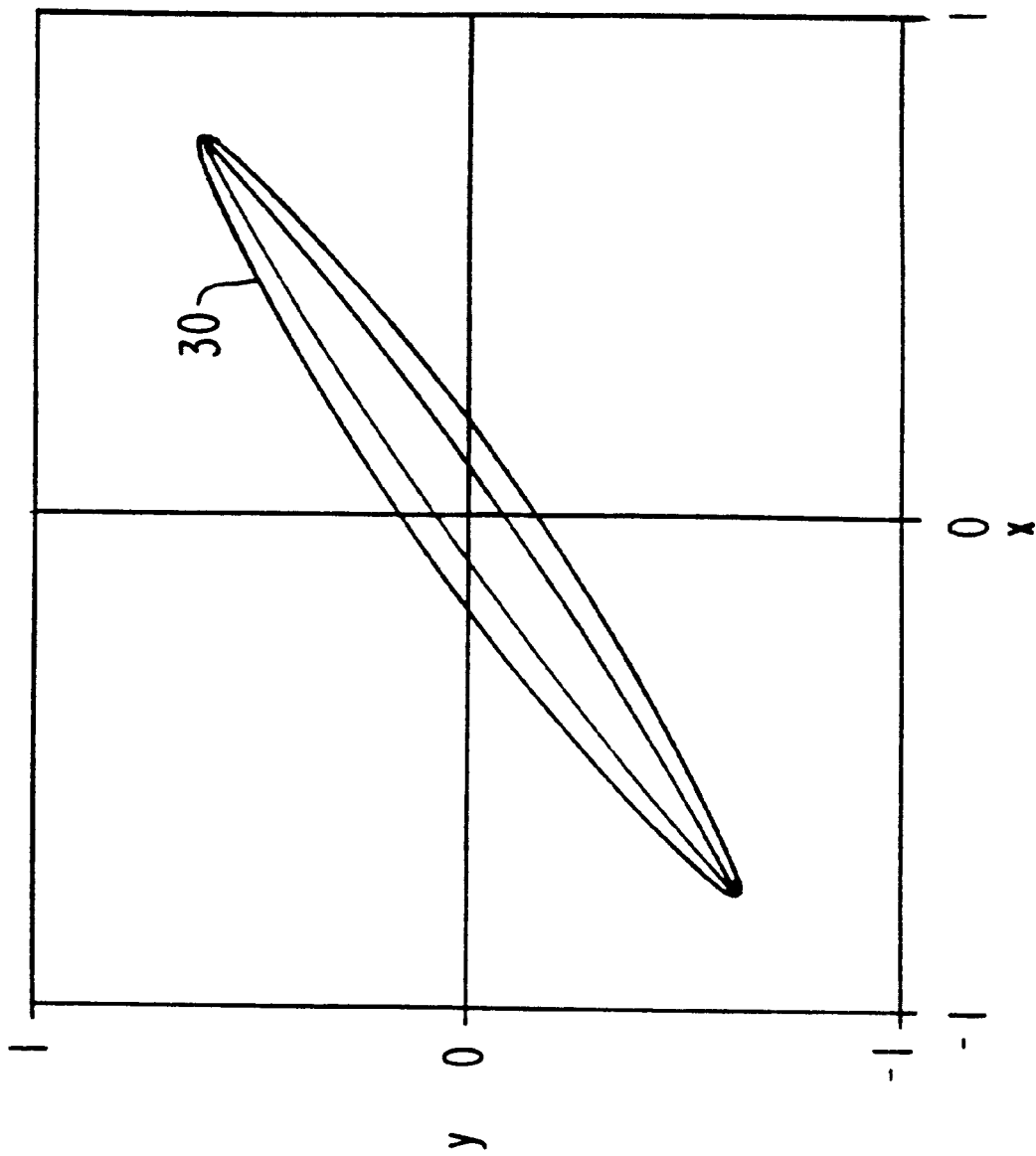
FIG. 3 shows the motion diagramed in FIG. 2 as a phase plot.
Figure 4:
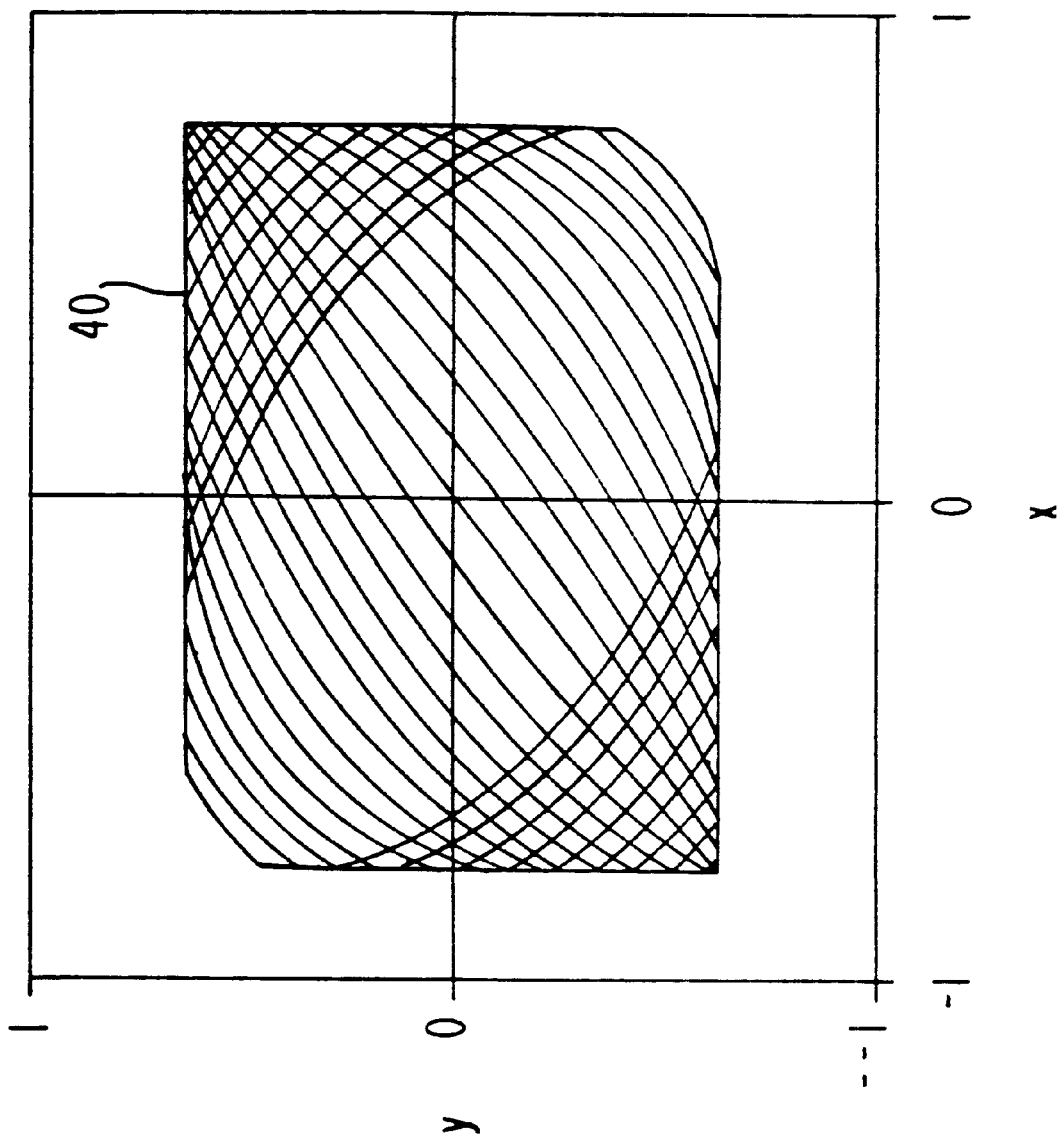
FIG. 4 shows the motion of the shaft as a phase plot, after fourteen oscillation cycles.

Ordinarily, the values of $k_1$ and $k_2$ are within about 5% of one another. FIG. 2 shows the normalized horizontal and vertical displacement of the vibrating tip of shaft 10 as a function of time over two oscillation cycles, with horizontal displacement (x) represented by the solid line 20 and vertical displacement (y) represented by the broken line 21, assuming the initial displacing force is imposed at an angle $\theta=40°$ to the horizontal. FIG. 3 shows the same displacement of the tip of shaft 10 as a phase plot 30, over two cycles, in x and y—i.e., FIG. 3 shows two cycles of the path the tip follows as it would be seen by an observer viewing the tip along the longitudinal axis of shaft 10, looking toward the handle end. FIG. 4 shows the phase plot 40 after fourteen cycles. Analysis of these observed motions yields the location of the planar oscillation plane—i.e., the angular orientation of shaft 10 in which, if the initial displacing force F were applied along that orientation, shaft 10 would oscillate substantially only along that orientation, with the tip tracing back and forth substantially along a line.

As seen in FIG. 4, the phase plot 40 of the tip motion after a sufficient number of cycles is substantially a rectangle. The orientation of the planar oscillation plane is that of one of the two orthogonal axes of that rectangle, where each axis of a rectangle is defined as a line midway between, and parallel to, a respective pair of sides of the rectangle. In the case of a true rectangle, it would be sufficient to determine the orientations of the sides, as the orientations of the sides and the axes, according to the definition just set forth, are identical. However, the phase plot 40 of the tip motion of a golf shaft may not be a true rectangle, unless one observes an infinite number of cycles, which is impractical because, first, it would not be commercially acceptable and, second, the oscillations of the golf club shaft ordinarily damp out before a true rectangle could be observed. Therefore, the orientation of each of the two axes may be calculated by assuming that lines drawn through the four vertices of the quasi-rectangular shape of the phase plot are the diagonals of the rectangle.

Having found the two axes of the rectangle, it is desirable to determine which one is the major axis, which may correspond to the principal planar oscillation plane, and which is a minor axis—i.e., one of one or more unstable planar oscillation planes. This can be determined rigorously by measuring the oscillation frequencies along those two axes, as described below. The major axis would be expected to correspond to the principal planar oscillation plane if the shaft was caused to vibrate along a direction determined by measuring the load on the deflected shaft as function of angle, and choosing the angle of maximum load as the direction in which to vibrate the shaft. It should be noted that this "load test" could be carried out by clamping either the tip or distal end, or the handle or proximal end, of the shaft, and measuring the load as a function of angle with the unclamped end deflected. In addition, the subsequent steps of locating the planar oscillation plane can be carried out with either end clamped and the unclamped end deflected. However, the subsequent steps of locating the planar oscillation plane preferably are carried out with the handle or proximal end clamped, and therefore the load test preferably is carried out that way as well. It should also be noted that if the load test is not carried out, one may find a planar oscillation plane, but that planar oscillation plane likely will not be the principal planar oscillation, plane.

Figure 5:
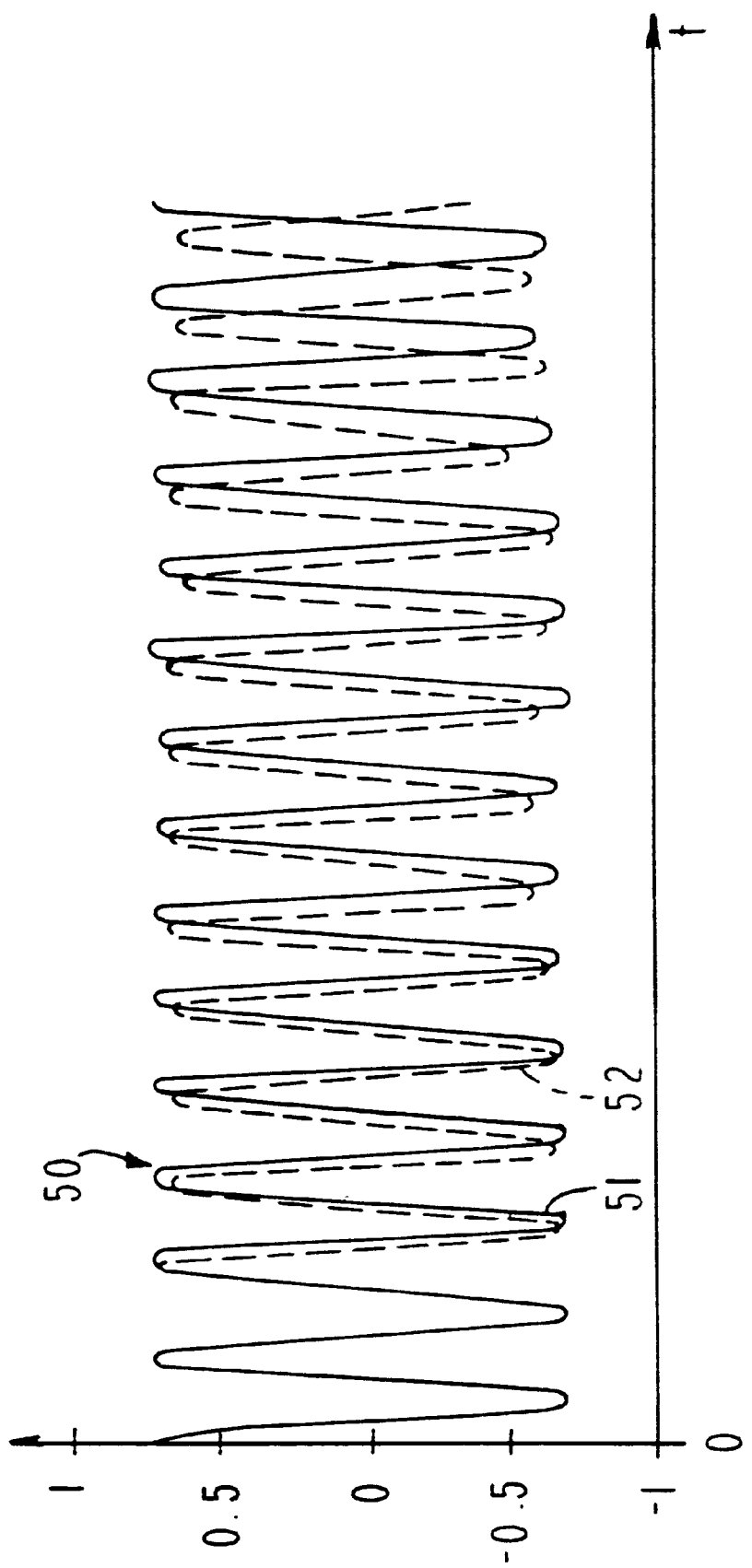
FIG. 5 shows the motion diagramed in FIG. 4, but as a function of time.

FIG. 5 shows a plot 50 of tip oscillation as a function of time, with a separate trace 51 for oscillations measured along the horizontal (x) axis and a separate trace 52 for oscillations measured along the vertical (y) axis. From these traces, frequency can be determined—e.g., graphically by counting the positive-going zero crossings. However, these horizontal and vertical axes x and y are offset from the planar oscillation plane by an angle determined as described above. If that angle is denoted θ, then the frequencies along these axes x and y as determined from the plot in FIG. 5 can be transformed into the coordinate system of the golf club shaft, having axes x' and y' that correspond to a stable planar oscillation plane and one of one or more unstable planar oscillation planes, as follows, where $f_1$ is the frequency at an angle θ from the x-axis—i.e., along the x'-axis, and $f_2$ is the frequency at an angle θ from the y-axis (θ+90° from the x-axis)—i.e., along the y'-axis:

$$f_1 = \left| \frac{f_x f_y (-f_y^2 \cos^2\theta + 2f_y^2 \cos^4\theta - 3f_x^2 \cos^2\theta + 2f_x^2 \cos^4\theta)^{0.5}}{f_y^2 \cos^2\theta + f_x^2 \cos^2\theta - f_x^2} \right|$$

$$f_2 = \left| \frac{f_x f_y (f_y^2 - 3f_y^2 \cos^2\theta + 2f_y^2 \cos^4\theta - f_x^2 \cos^2\theta + 2f_x^2 \cos^4\theta)^{0.5}}{f_y^2 \cos^2\theta + f_x^2 \cos^2\theta - f_x^2} \right|$$

If $f_1$ is greater than $f_2$, then one of the stable planar oscillation planes of the golf club shaft is at an angle θ with respect to the x-axis. If $f_1$ is less than $f_2$1 then one of the stable planar oscillation planes of the golf club shaft is at an angle θ with respect to the y-axis—i.e., θ+90° with respect to the x-axis. If the load test has been performed and used to determine the initial angle of vibration, than the stable planar oscillation plane so located can be expected to be the principal planar oscillation plane.

Although this mathematical technique, for determining which of the planar oscillation planes already identified is the principal planar oscillation plane, is rigorous and precise, it is more computationally intensive than is necessary in view of the objective. Therefore, in another preferred embodiment of the invention, as described above and in more detail below, the location of the principal planar oscillation plane is located to a first-order approximation—i.e., at least to within the correct quadrant—by determining the orientation of the direction of greatest resistance to bending or twisting of the golf club shaft. This has the further benefit of quickly identifying the "forward" direction of the principal planar oscillation plane, as described above.

A preferred embodiment of apparatus 60 for implementing the present invention is shown in FIGS. 6–13. Although apparatus 60 could be made to implement the rigorous mathematics set forth above, it has been determined in practice that a simpler iterative process as described below achieves acceptable results at lower cost. Therefore, in a particularly preferred embodiment, apparatus 60 uses that simpler process.

Figure 6:
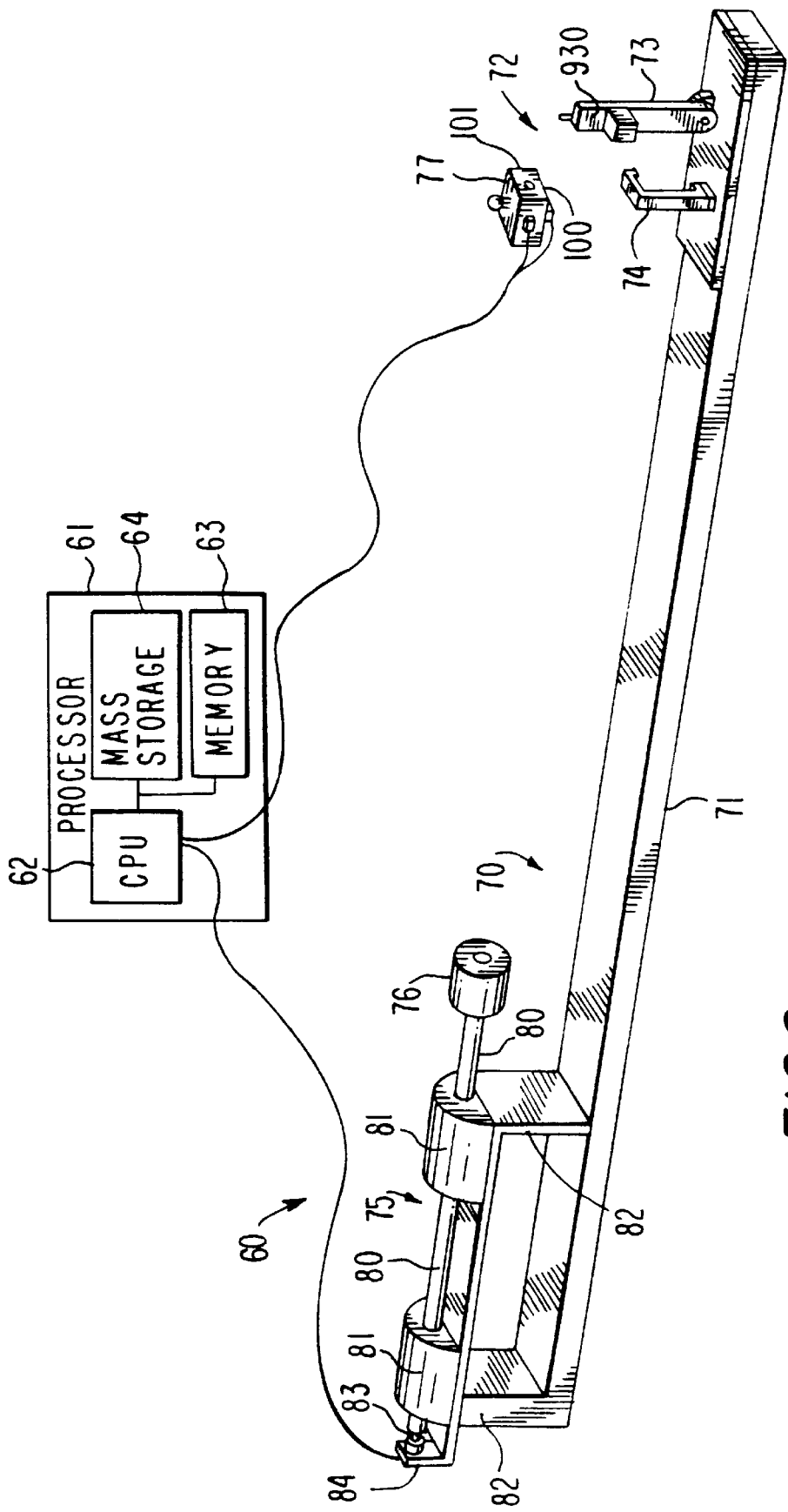
FIG. 6 is a perspective view of apparatus according to the present invention for determining the preferred orientation of a golf club shaft.
Figure 7:
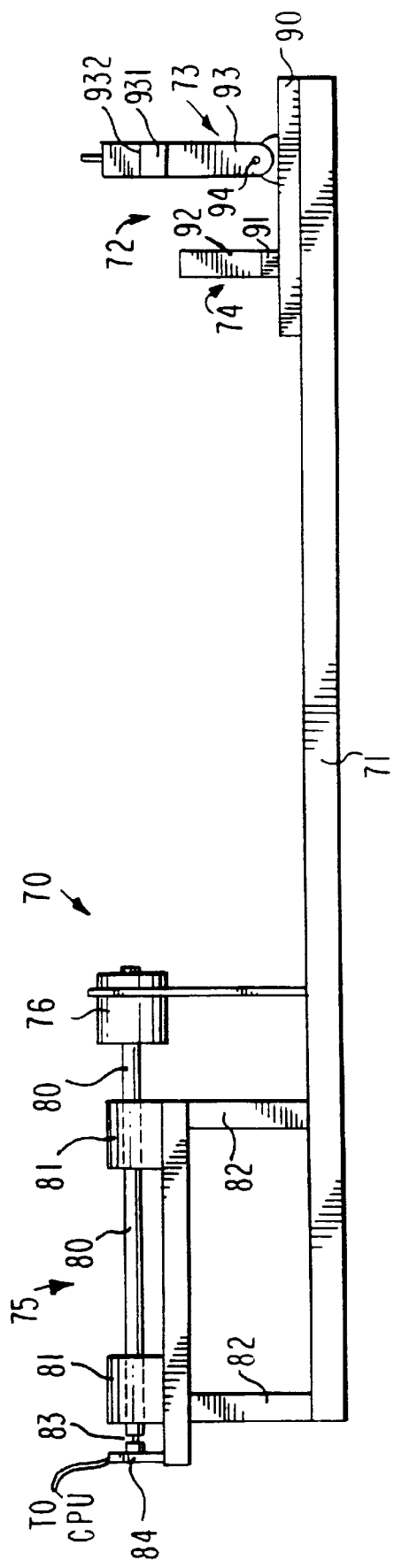
FIG. 7 is a perspective view of a shaft testing assembly of the apparatus of FIG. 6.

In the preferred embodiment, apparatus 60 includes shaft testing assembly 70 and processing unit 61. Processing unit 61 can be any system capable of processing input data from sensors 77 and 74 of shaft testing assembly 70 and performing either the rigorous mathematical calculations described above or the simpler iterative calculations described below. As shown in FIG. 6, processor 61 is preferably a general purpose computer such as a personal computer, which may, e.g., be based on a PENTIUM® central processing unit (CPU) 62 available from Intel Corporation, of Santa Clara, Calif., running a version of the WINDOWS® operating system available from Microsoft Corporation, of Redmond, Washington, and programmed with software as described below. However, processor 61 could also be hard-wired circuitry or one or more programmed programmable logic devices dedicated to the functions necessary to locate the spine of a golf club shaft. In any event, processor 61 preferably also includes memory 63 and mass storage 64.

Shaft testing assembly 70 preferably includes an elongated base 71, which is at least as long a golf club shaft. At one end of base 71 is a measurement assembly 72, including a deflector assembly 73 and a deflection load sensor 74. At the other end of base 71 is a shaft holding and rotating assembly 75, including a rotatable chuck 76 for holding a golf club shaft. Apparatus 60 also includes a tip mass and sensor assembly 77 which during testing of a golf club shaft is mounted on the distal end of the golf club shaft and cooperates with deflector assembly 73.

Figure 8:
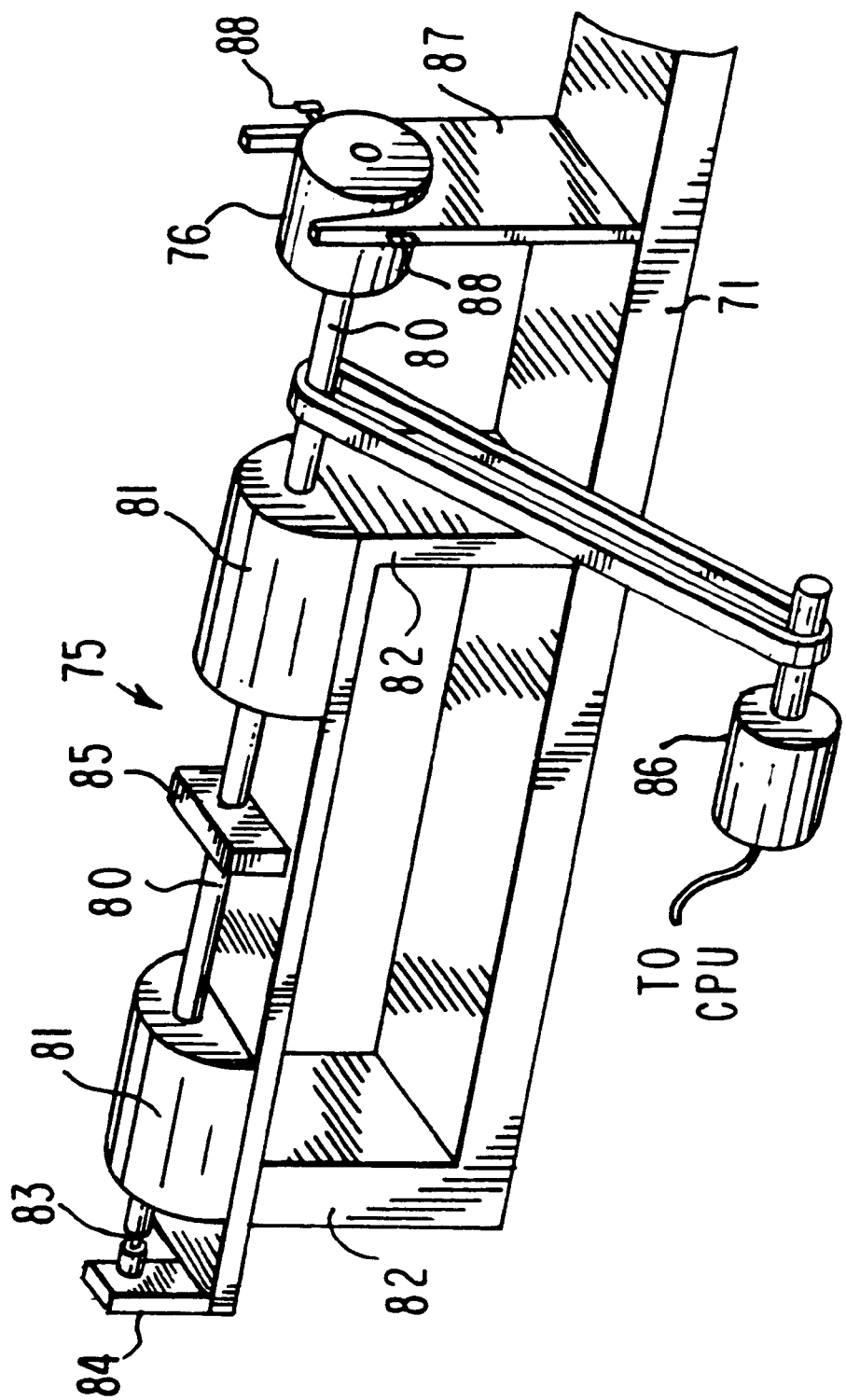
FIG. 8 is a perspective view of a shaft holding and rotating assembly of the apparatus of FIGS. 6 and 7.

As seen in FIG. 8, shaft holding and rotating assembly 75 preferably includes rotatable chuck 76 which preferably may be conventional, preferably holding a golf club shaft by exerting radially inward force substantially evenly around the shaft circumference. Chuck 76 preferably is mounted at the end of axle 80, which preferably is journalled in bearings 81. Bearings 81 preferably are mounted on supports 82 so that the axis of rotation of axle 80, and by extension that of chuck 76 and the golf club shaft being tested, is at a predetermined height above base 71. The end of axle 80 remote from chuck 76 preferably is connected via universal joint 83 to a potentiometer 84 that is used as an angular position sensor as described below. Universal joint 83 prevents any slight misalignment between the axis of axle 80 and the shaft of potentiometer 84 from damaging potentiometer 84. Similarly, a traveling nut 85 preferably is provided on axle 80 to act as a rotational stop to limit rotation of axle 80 and thereby prevent damage that might result from overrotation of potentiometer 84. An optional motor 86 may be provided to rotate chuck 76, although manual rotation can also be used. In addition it is preferable to provide a clamp 87 to minimize vibrations of chuck 76 as it rotates. Clamp 87 preferably provides a friction fit to chuck 76 that is just light enough to allow rotation of chuck 76. Screws 88 may be provided to adjust the jaw of clamp 87.

Figure 9:
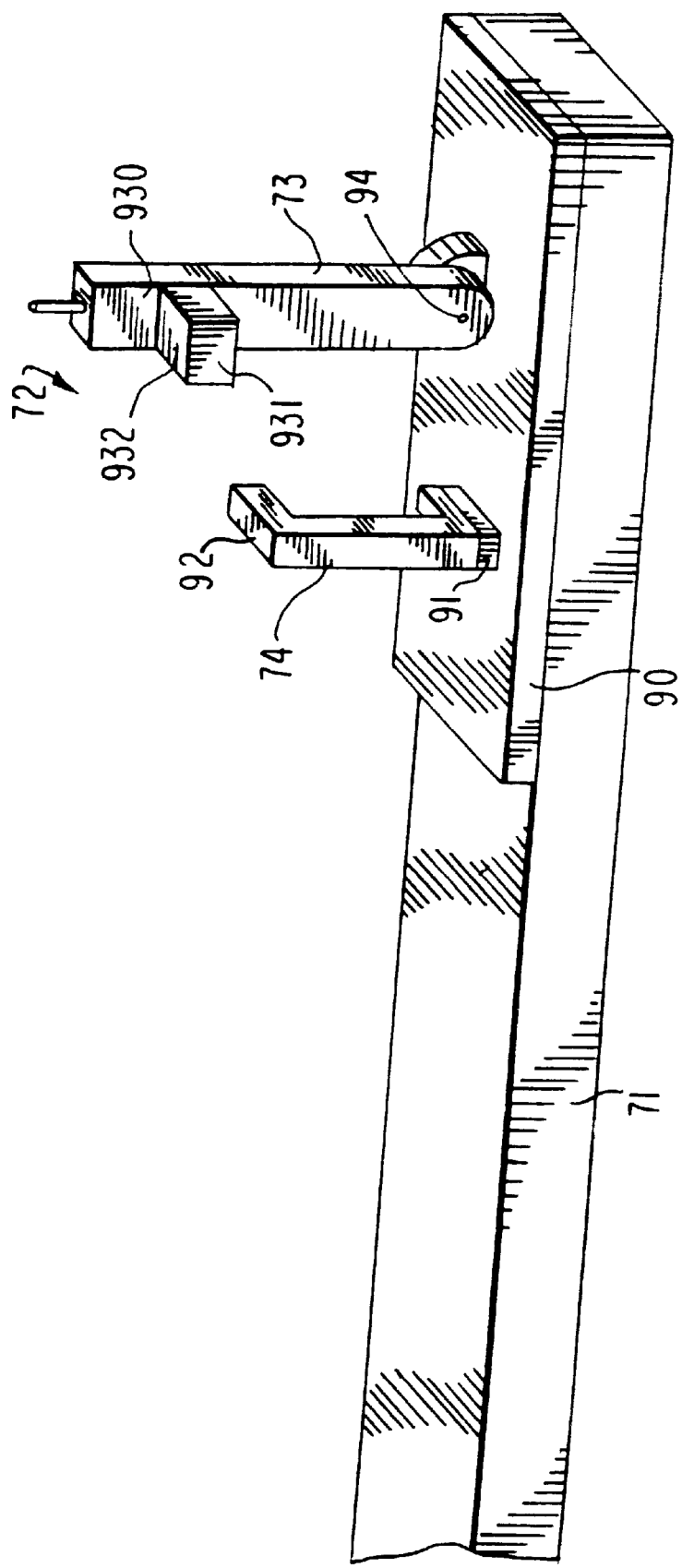
FIG. 9 is a perspective view of a measurement assembly of the apparatus of FIGS. 6–8.

As seen in FIG. 9, measurement assembly 72 includes a base plate 90 that is mounted to base 71. A load cell 91, such as a Model LCAE-2KG, available from Omega Engineering, Inc., of Stamford, Conn., is mounted to base plate 90, and a shaft tip restraining arm 92 is mounted to load cell 91 on the side of load cell 91 opposite base plate 90, for a purpose to be described below. Measurement assembly 72 also preferably includes a deflector arm 93 pivotably mounted to base plate 90. Preferably, deflector arm 93 is mounted so that at least one side 930 thereof is substantially perpendicular to base plate 90, and so that it pivots about an axis 94 that is substantially parallel to base plate 90.

Deflector arm 93 preferably has a projection 931, preferably extending from side 930 thereof. Projection 931 preferably has a surface 932 facing away from axis 94 that bears substantially the same angular relationship to side 930 as does side 100 of tip mass and sensor assembly 77 to side 101 of tip mass and sensor assembly 77, for reasons described below.

Figure 10:
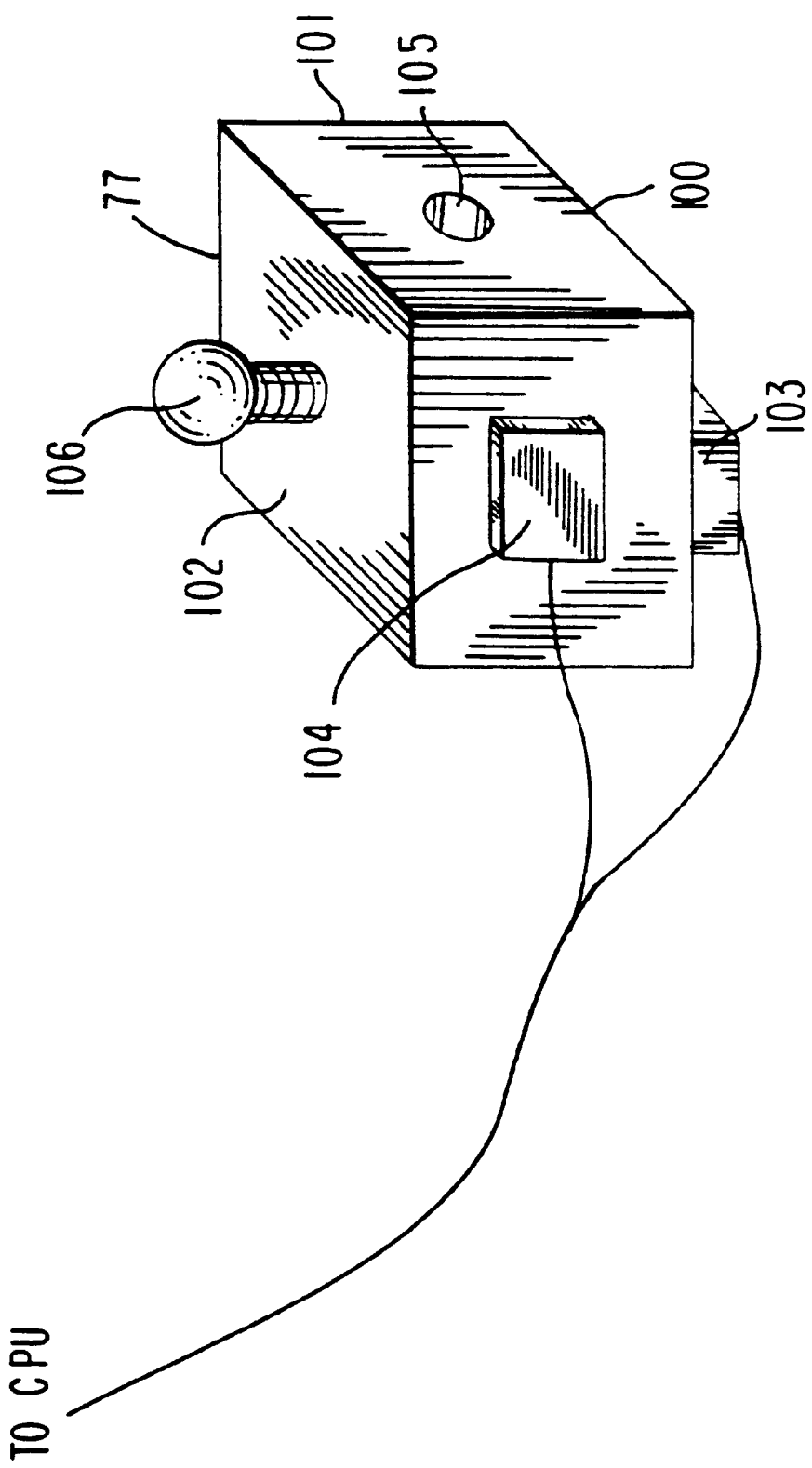
FIG. 10 is a perspective view of a tip mass and sensor assembly of the apparatus of FIGS. 6–9.

As shown in FIG. 10, tip mass and sensor assembly 77 preferably has a body 102 with a mass of between about 190 grams and about 220 grams, and preferably about 200 grams, to simulate the mass of a golf club head at the distal end of a golf club shaft. In another embodiment, different tip masses could be provided to more closely simulate different types of club heads, which have different masses. However, this latter embodiment would be more costly, insofar as each different mass would need its own set of transducers to collect displacement data, as well as different computations based on those data.

The presence of body 102 on the end of a golf club shaft when the shaft is deflected and allowed to oscillate during testing in accordance with the present invention, as described below, not only mimics the effect of a club head during a swing, but also provides "reaction mass" that prevents the shaft oscillations from damping out before sufficient data can be collected. The transducers that collect the displacement data preferably are two accelerometers 103, 104—such as Model 8303A available from Kistler Instrument Corp. of Amherst, N.Y.—aligned along two different axes. Preferably, the two axes are orthogonal to one another, but that is not necessary; as long as the angular relationship between the axes is known, the motion recorded by accelerometers 103, 104 can be resolved computationally into two orthogonal components. Also preferably, the two axes are parallel and perpendicular, respectively, to base 71. Again, however, that is not necessary.

Tip mass and sensor assembly 77 preferably has an attachment structure for attaching to the tip of a golf club shaft. Preferably, the attachment structure includes a bore 105, slightly larger in diameter than an average golf club shaft, in body 102, into which the shaft may be introduced, and a set screw 106 for tightening body 102 onto the shaft.

Alternatively, some sort of quick-release clamp can be provided, particularly for use in an automated system as described below.

As discussed above, there preferably is the same relationship between the orientations of sides 100, 101 of tip mass and sensor assembly 77 as there is between surfaces 930, 932 of deflector arm 93. This is so that tip mass and sensor assembly 77 can be repeatedly lined up the same way for every test, by resting sides 100, 101 against surfaces 930, 932.

Figure 11:
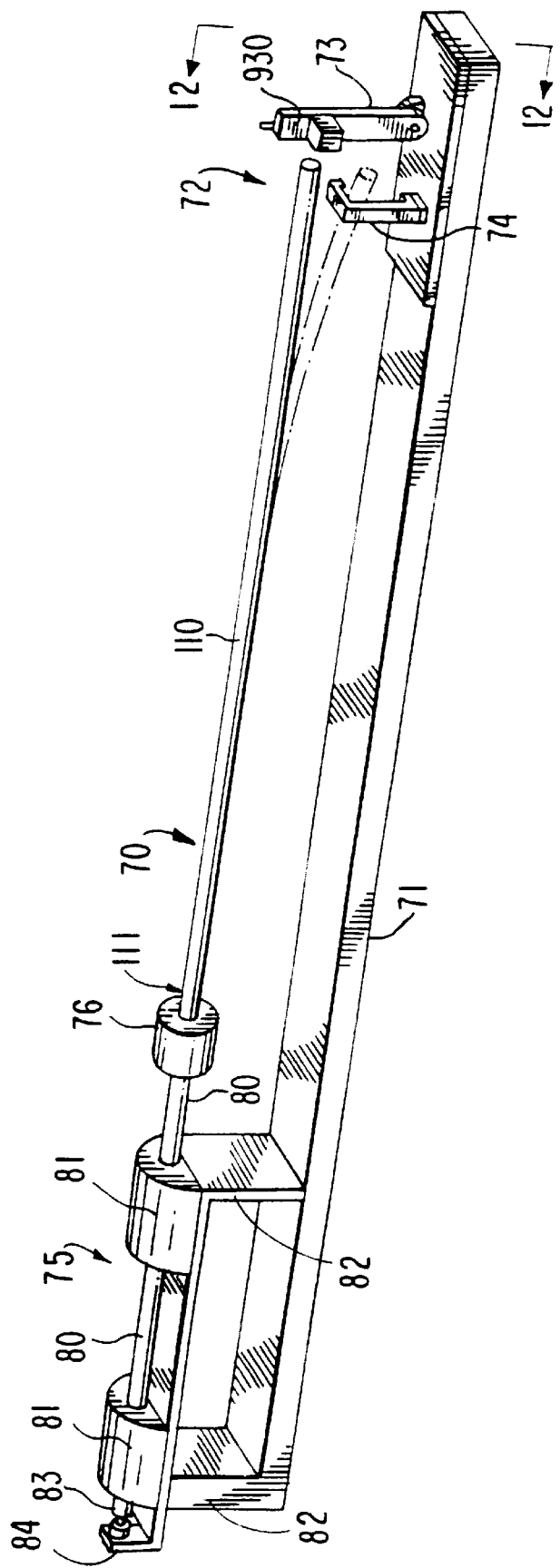
FIG. 11 is a view similar to FIG. 7 with a golf club shaft mounted in the apparatus.

In order to test a golf club shaft, the shaft 110 is mounted in chuck 76 as shown in FIG. 11. The tip, or distal end, of shaft 110 is then deflected and restrained under the lip 120 of shaft tip restraining arm 92, as shown in phantom in FIG. 11, so that the restoring force tending to straighten shaft 110 can be measured by load cell 91. Chuck 76 is then rotated—manually, or by motor 86 preferably under control of processor 61—while the restoring force is recorded by computer 61 as a function of angle, which is determined by potentiometer 84, to which a known voltage is applied. By well-known voltage divider techniques, the changing resistance is translated to a changing voltage, which can be converted to an angle.

It might be expected that when the upward restoring force is a maximum, then the point of maximum asymmetry of the shaft, representing the hard side of the principal planar oscillation plane, is facing upward. It has been found empirically, however, that that is not so, but that the hard side is within the quadrant that is facing upward when the maximum force is measured. The angle of the maximum force is therefore recorded in this static portion of the test, and the remainder of the test, which is dynamic, is conducted.

In the dynamic portion of the test, the tip or distal end of golf shaft 110 is oscillated with tip mass and sensor assembly 77 in place. While in the static portion of the test the tip preferably is deflected vertically, in the dynamic portion of the test the deflection is preferably horizontal, although any direction can be used in either portion of the test. The reason for preferring horizontal deflection in the dynamic portion of the test is that, first, the effect, on the results, of gravity acting on the tip mass is minimized, and, second, it is easier to oscillate the shaft without it hitting base 71. Therefore, before the dynamic portion of the test is initiated, chuck 76 preferably is rotated about 90°, so that the estimated orientation of the spine, or principal planar oscillation plane, which had been vertical, is now horizontal.

In the apparatus so far described, tip mass and sensor assembly 77 is applied, and a horizontal impulse is imparted, to golf club shaft 110, as follows. With the proximal or handle end 111 of golf club shaft 110 held in chuck 76, and deflector arm 93 standing erect, bore 105 in body 102 of tip mass and sensor assembly 77 is placed over distal or tip end 112 of golf club shaft 110. Tip mass and sensor assembly 77 is then manipulated until surfaces 100, 101 of body 102 are firmly seated against surfaces 930, 932 of deflector arm 93, placing accelerometers 103, 104 in their predetermined desired orientations. A portion of surface 100 not occupied by accelerometer 103 is used for this purpose, so that accelerometer 103 does not interfere with the seating of body 102. Although accelerometers 103, 104 are shown connected to processor 61 by wires 62, a wireless connection (not shown) could be provided.

Figure 12:
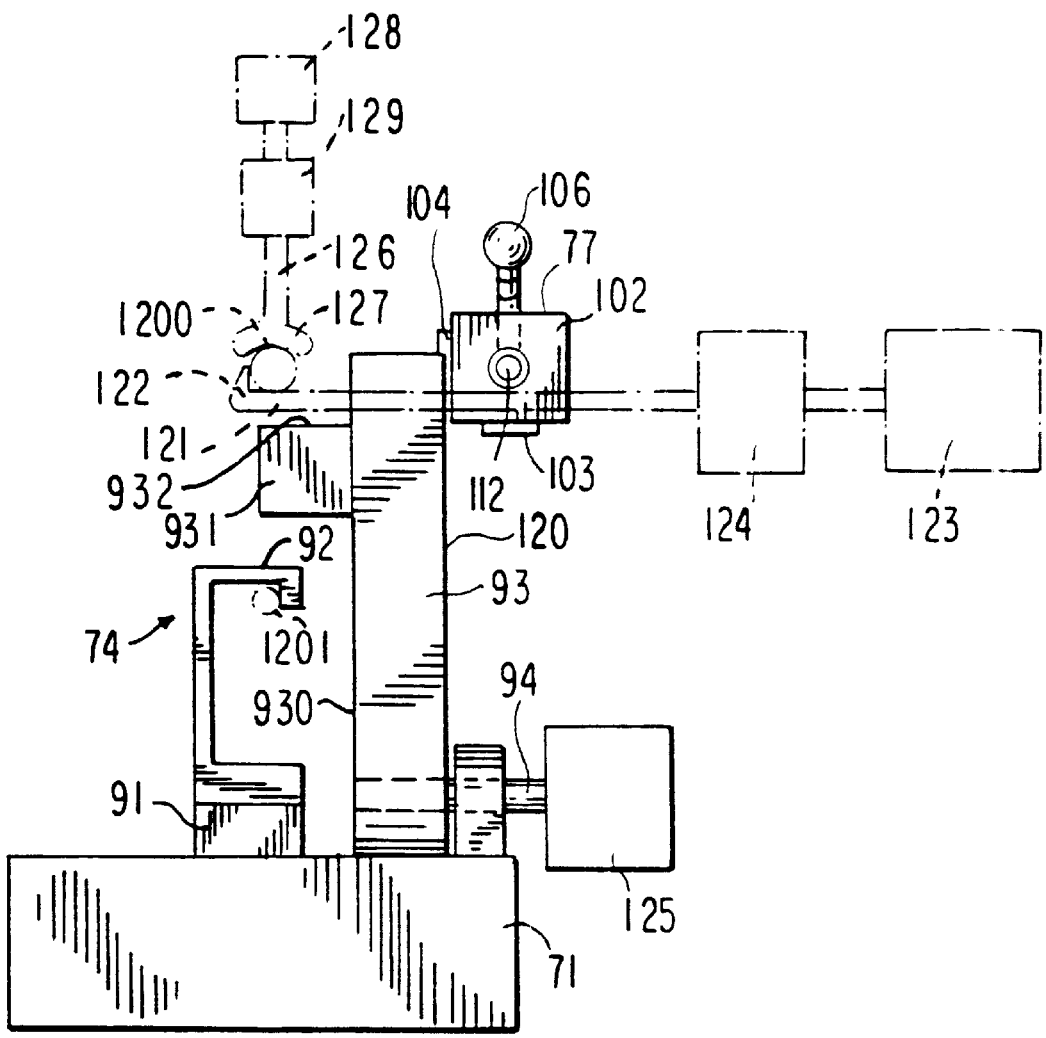
FIG. 12 is an end elevational view, taken from line 12—12 of FIG. 11, but with the golf club shaft deflected in preparation for oscillation according to the invention.

A preferably substantially horizontal impulse is provided to tip mass and sensor assembly 77 by deflecting tip 112 of golf club shaft 110 to side 120 of deflector arm 93 opposite side 930, as seen in FIG. 12, and then, preferably in a sudden motion, pivoting deflector arm 93 out of its erect position, allowing the restoring force in deflected golf club shaft 110 to provide a horizontal impulse to start tip 112 of golf club shaft 110 to begin vibrating, along with tip mass and sensor assembly 77, in the manner described above in connection with FIGS. 2–5.

Although the initial deflection of golf club shaft 110 behind deflector arm 93, as well as the pivoting of deflector arm 93 to allow tip 112 to oscillate, can be accomplished manually, they can also be accomplished automatically. Thus, an arm 121 bearing a finger 122, driven by a motor 123 through suitable gearing or linkage 124 that provides the necessary horizontal and vertical components of motion, can be used to move tip 112 of golf club shaft 110 from its neutral position 1200 to the position behind deflector arm 93. This could involve both vertical and horizontal movement of tip 110 by finger 122, or finger 122 could move solely horizontally while motor 125 pivots deflector arm 93 out of the way temporarily and then restores deflector arm 93 to the erect position. Similarly, the pivoting of deflector arm 93 to allow oscillation to begin can be performed by motor 125 instead of manually.

As a further alternative, instead of applying an impulse by deflecting shaft 110 behind deflector arm 93 and then releasing arm 93, a horizontal plunger or ram (not shown) could be used to strike tip mass and sensor assembly 77 rapidly and for a short time.

Each of accelerometers 103, 104 records acceleration in one of two respective directions, which preferably are orthogonal to one another, and preferably are horizontal and vertical, respectively. However, any two directions may be used, as long as they are known, and the horizontal and vertical components can be calculated. The accelerations preferably are integrated over time to determine horizontal and vertical displacements. Alternatively, displacement can be measured directly, for example, by providing, instead of accelerometers 103, 104, a light source, such as a laser or light-emitting diode (not shown), on the end of tip mass and sensor assembly 77 emitting light along the direction of the longitudinal axis of golf club shaft 110. A light sensitive detector array (also not shown) could be placed substantially perpendicular to the emitted light beam, which would trace the displacement of tip 112 on the detector array, recording the displacement directly. Regardless of how the data are collected, they can be plotted as a function of time and used to derive displacement and frequency data that are then used, as described above, to mathematically determine the preferred angular orientation in which lies the planar oscillation plane. The direction of the planar oscillation plane closer to the estimated orientation determined by load cell 91 would be considered the "hard" side of the principal planar oscillation plane or spine of golf club shaft 110, which preferably should be aligned perpendicular to, and facing, or in any other predetermined orientation with respect to, the club head face. However, the load cell test could be eliminated, insofar as aligning golf club shaft 110 with the planar oscillation plane in a desired orientation with respect to the club head face, whether the hard side of the planar oscillation plane faces toward or away from the face, is better than having the planar oscillation plane at a random orientation relative to the club head face, and also insofar as aligning any planar oscillation plane with respect to the club head face, even if it is not the principal planar oscillation plane, is better than a random orientation. It should be remembered, however, that if a random planar oscillation plane, rather than the principal planar oscillation plane, is found for each golf club shaft in a set, then even if the planar oscillation plane so found for each shaft is oriented similarly relative to its respective club head, the set cannot be assumed to be uniformly oriented.

Figure 13:
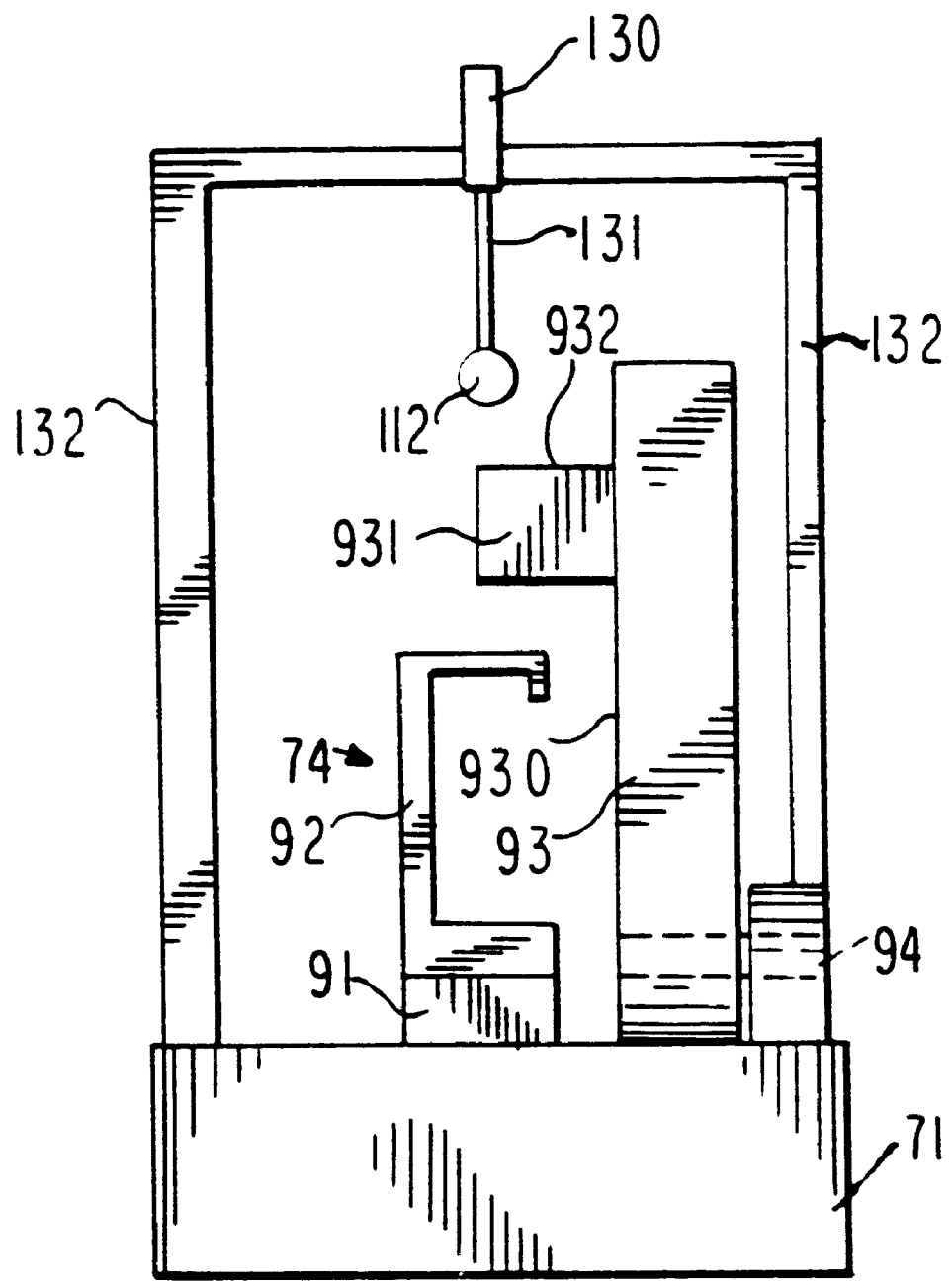
FIG. 13 is perspective view of the apparatus of FIGS. 6–10 with a marking assembly included.
Figure 14:
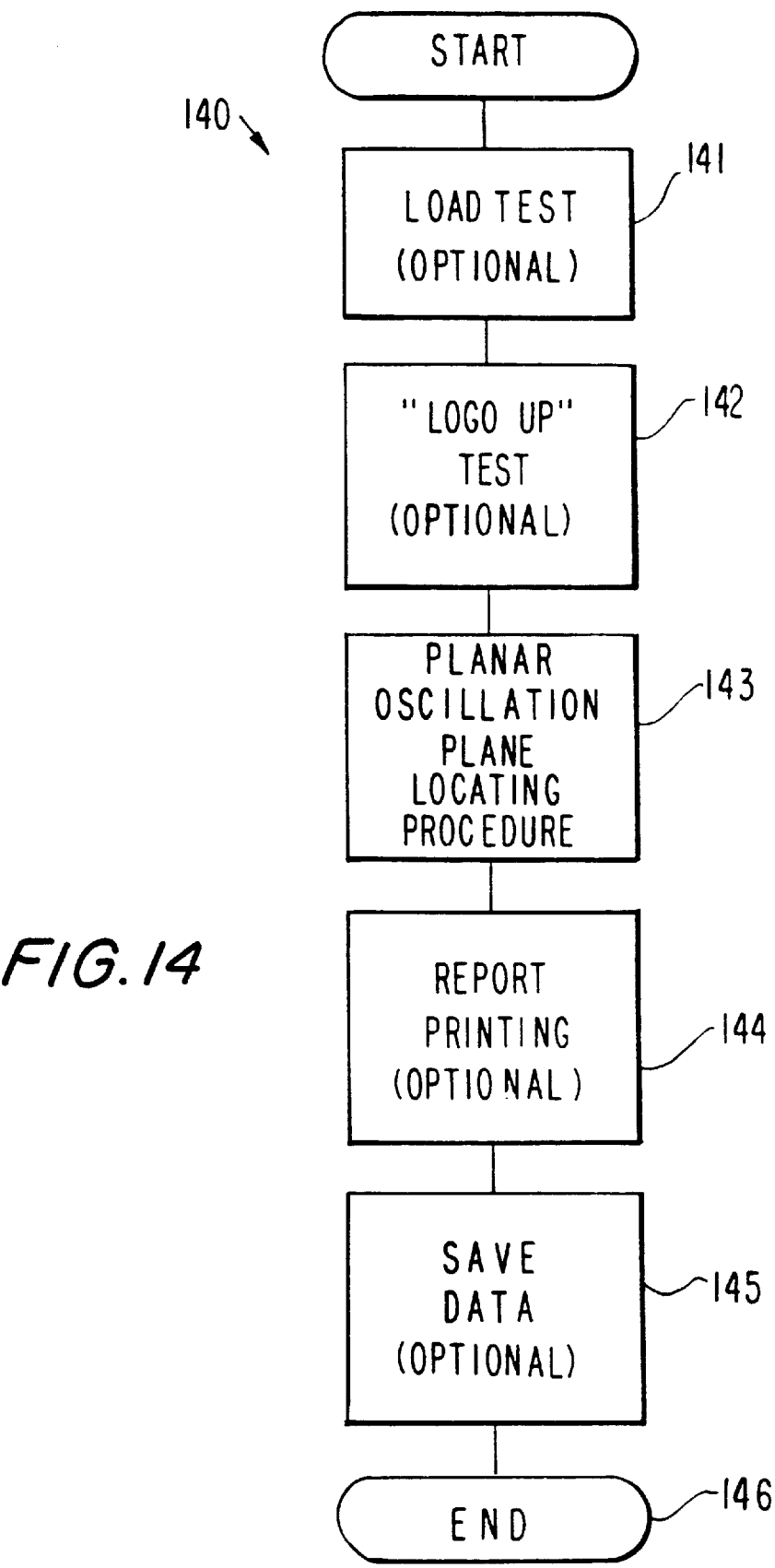
FIG. 14 is a flow diagram of a preferred embodiment of a method according to the invention for location the preferred orientation of a golf club shaft.

Once the location of the spine has been determined, shaft 110 preferably is marked to indicate the orientation of the spine, or at least of the planar oscillation plane. Marking may be accomplished by applying a pigment (e.g., paint or ink) to the surface of shaft 110. For example, an ink marker 130 having a marking tip 131 could be mounted on a frame 132 as shown in FIG. 13. After the preferred orientation has been determined, shaft 110 can be rotated so that the preferred orientation is aligned with marking tip 131, which then applies a mark to shaft 110. Alternatively, 130 could represent a paint reservoir, while 131 would represent a paintbrush. As a further alternative, marking of shaft 110 could be accomplished using a directed energy beam or a particle beam to etch a marking into the surface of shaft 110. In such an alternative, 130 could represent a high-energy laser, while 131 would represent the laser beam, or 130 could represent an electron gun while 131 would represent the electron beam. Optionally, either shaft 110 or the marking assembly could be moved parallel to the shaft longitudinal axis so that the marking on the shaft is a line instead of a dot, to increase its visibility.

The preferred method 140 according to the invention for locating the preferred orientation (i.e., either any planar oscillation plane or the principal planar oscillation plane or "spine"), using apparatus 60, is diagramed in FIGS. 14–17. Method 140 preferably starts with load test 141, described above, which uses load cell 91 to estimate the orientation of the principal planar oscillation plane and which at least identifies which of the two sides of the principal planar oscillation plane is the "hard" side of the planar oscillation plane. Load test 141 could be omitted, but only if one is prepared to find any planar oscillation plane, rather than the principal planar oscillation plane in particular. Where load test 141 is performed, the result is used as a starting point for planar oscillation plane location step 143, below. Alternatively, load test 141 could be performed on a stand-alone basis to measure the symmetry of a shaft.

After load test 141 is performed, optional "logo up" test 142 is performed. Conventional golf clubs are typically assembled with the manufacturer's logo, which is printed on the shaft, facing toward the club head face, in what is referred to as a "logo up" configuration (some manufacturers align the logo 180° away from the club head face in a "logo down" configuration, or in other configurations). Because the logo is printed at a random location on the shaft circumference, the "logo up" alignment is purely random. Logo up test 142 merely gathers data regarding the oscillation of a golf club shaft in its factory installed orientation.

As described above, planar oscillation plane location procedure 143 is performed next. After procedure 143 has been performed, an optional report printing step 144, in which some or all of various parameters regarding the golf shaft whose preferred orientation has been found are printed. Finally, in an optional save step 145, various of the data acquired during steps 141–144 are saved (e.g., in mass storage 64).

Figure 15:
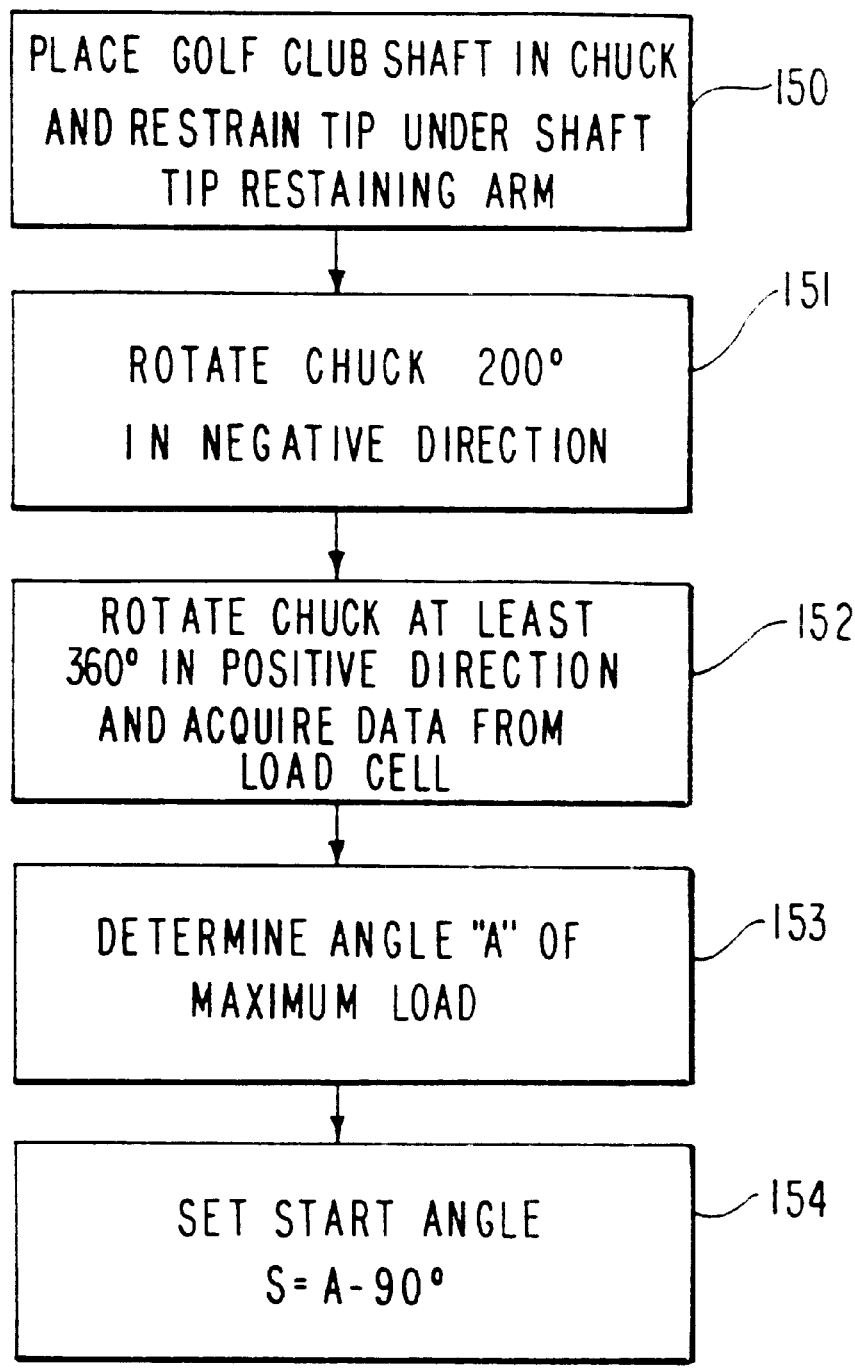
FIG. 15 is a flow diagram of a load test performed according to the invention as part of the method of FIG. 14.

Load test 141 is shown in more detail in FIG. 15. At step 150, a golf club shaft 110, which may have been removed from a golf club, is placed in chuck 76 at an arbitrary starting angle. Tip 112 of golf club shaft 110 is deflected and restrained under shaft tip restraining arm 92 so that the restoring force in the deflected shaft 110 is measured by load cell 91. The shaft can be deflected and secured manually, or the deflection and securing can be accomplished automatically. Thus, an arm 126 bearing a finger 127, driven by a motor 128, through suitable gearing or linkage 129 that provides the necessary horizontal and vertical components of motion, can be used to move tip 112 of golf club shaft 110 from its neutral position 1200 to position 1201 under shaft tip retention arm 92.

Once tip 112 is under shaft tip retention arm 92, then in step 151 chuck 76 preferably is rotated about 200° in one direction (which may be designated the negative rotation direction). Next, at step 152, chuck 76 is rotated at least 360° in the opposite direction (which may be designated the positive rotation direction) while data is acquired from load cell 91 and recorded as a function of angle. Preferably, in step 152, chuck 76 is rotated about 400° and 40° (preferably the first and last 20°) is discarded. Alternatively, however, the reverse rotation of step 151 may be omitted, as long as data are recorded through at least 360°, and if data are recorded through more than 360°, then any amount of rotation greater than 360° may be used and any portion—all at the beginning, all at the end, or any combination of beginning and end—may be discarded to provide 360° worth of data.

At step 153, the data gathered in step 152 are examined, and the angle A corresponding to the maximum load measured by load cell 91 is determined. If desired, the load as a function of angle may be graphed for display. Next, at step 154, the start angle S, for use in planar oscillation plane location test 143, is set to A-90°. This takes into account the change of orientation from vertical to horizontal as between the load test 141 and the planar oscillation plane location test 143, as described above.

Figure 16:
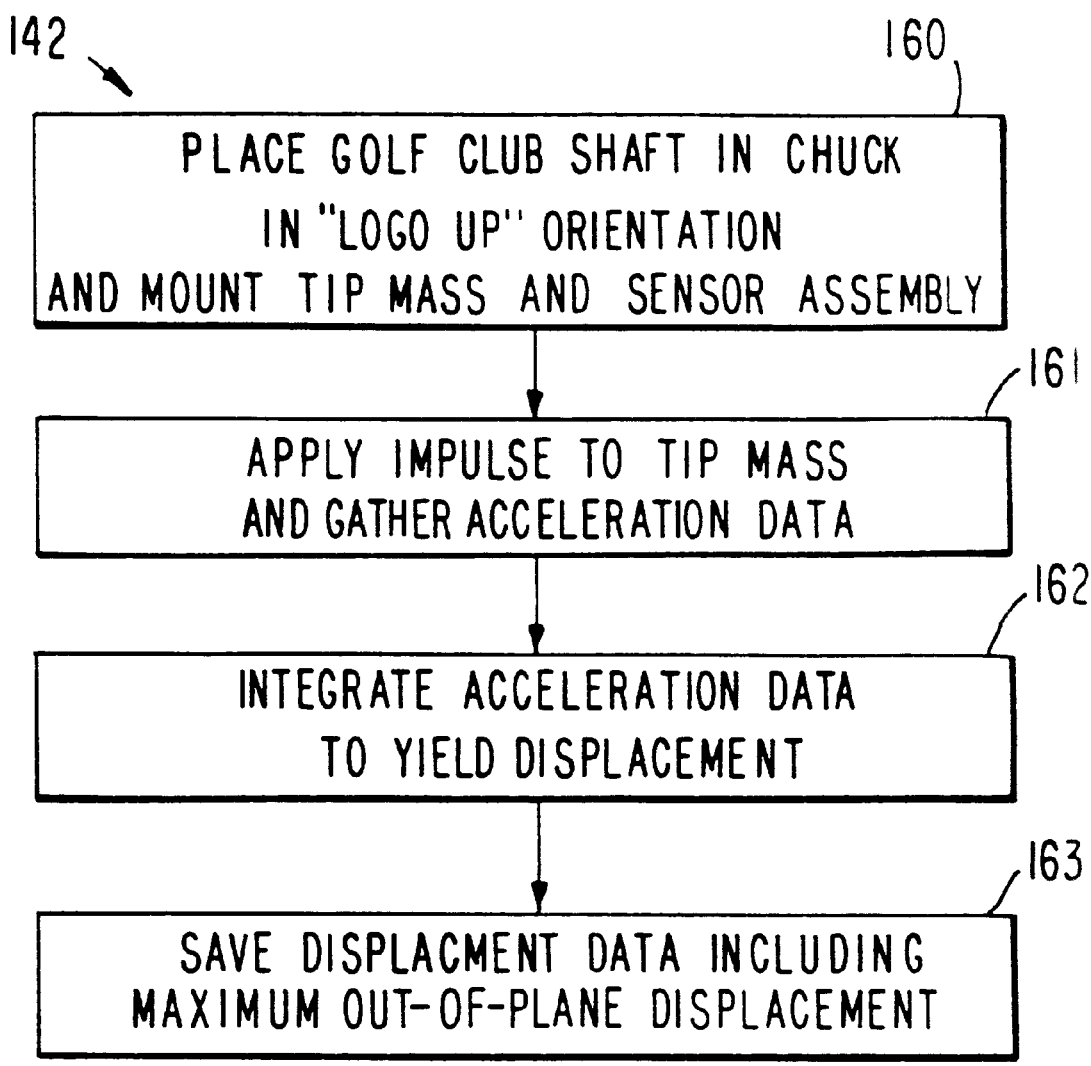
FIG. 16 is a flow diagram of a "logo up" comparison test performed according to the invention as part of the method of FIG. 14.

After the conclusion of load test 141, "logo up" test 142, shown in detail in FIG. 16, may be conducted. The purpose of "logo up" test is primarily to provide a "before" comparison to the "after" result to be obtained after performing planar oscillation plane location test 143. Therefore, as stated above, "logo up" test 142 is optional. In particular, while "logo up" test 142 may be used primarily as a promotional tool in an aftermarket situation—i.e., by a golf club refitter—to show the improvement obtained by realigning the shaft of a golf club in accordance with the invention, it probably would not be used by a golf club manufacturer who produces "spine-aligned" golf clubs, because there is no need to show comparative data.

"Logo up" test 142 begins at step 160 where golf club shaft 110, which, again, may have been removed from a golf club, is placed in chuck 76. If it had previously been part of a completed golf club, shaft 110 is placed in chuck 76 in the same orientation in which it was oriented in the golf club, as the club would have been positioned by a golfer adjacent a ball before the start of the golfer's swing. In most cases, this would be with the manufacturer's logo facing up, but sometimes the logo faces down or in a random direction. If test 142 is being performed on a golf club shaft that has never been part of a golf club, then preferably it is tested with its logo up. Tip mass and sensor assembly 77 is then mounted on tip 112 of shaft 110.

Next, at step 161, an impulse is applied to tip mass and sensor assembly 77 in one of the ways described above and orthogonal—preferably, horizontal and vertical—acceleration data are gathered, preferably for about 4 seconds. These data preferably are integrated at step 162 to yield orthogonal—preferably horizontal and vertical—displacement data as functions of time, which preferably are saved at step 163 for later comparison with the results after spine-alignment of shaft 110, and the data preferably also are graphed at step 163 for display to the owner of the golf club of which shaft 110 is a part. The maximum out-of-plane displacement—i.e., preferably the maximum vertical displacement—preferably is also saved at step 163 for display to the owner. Test 142 is now complete.

Figure 17:
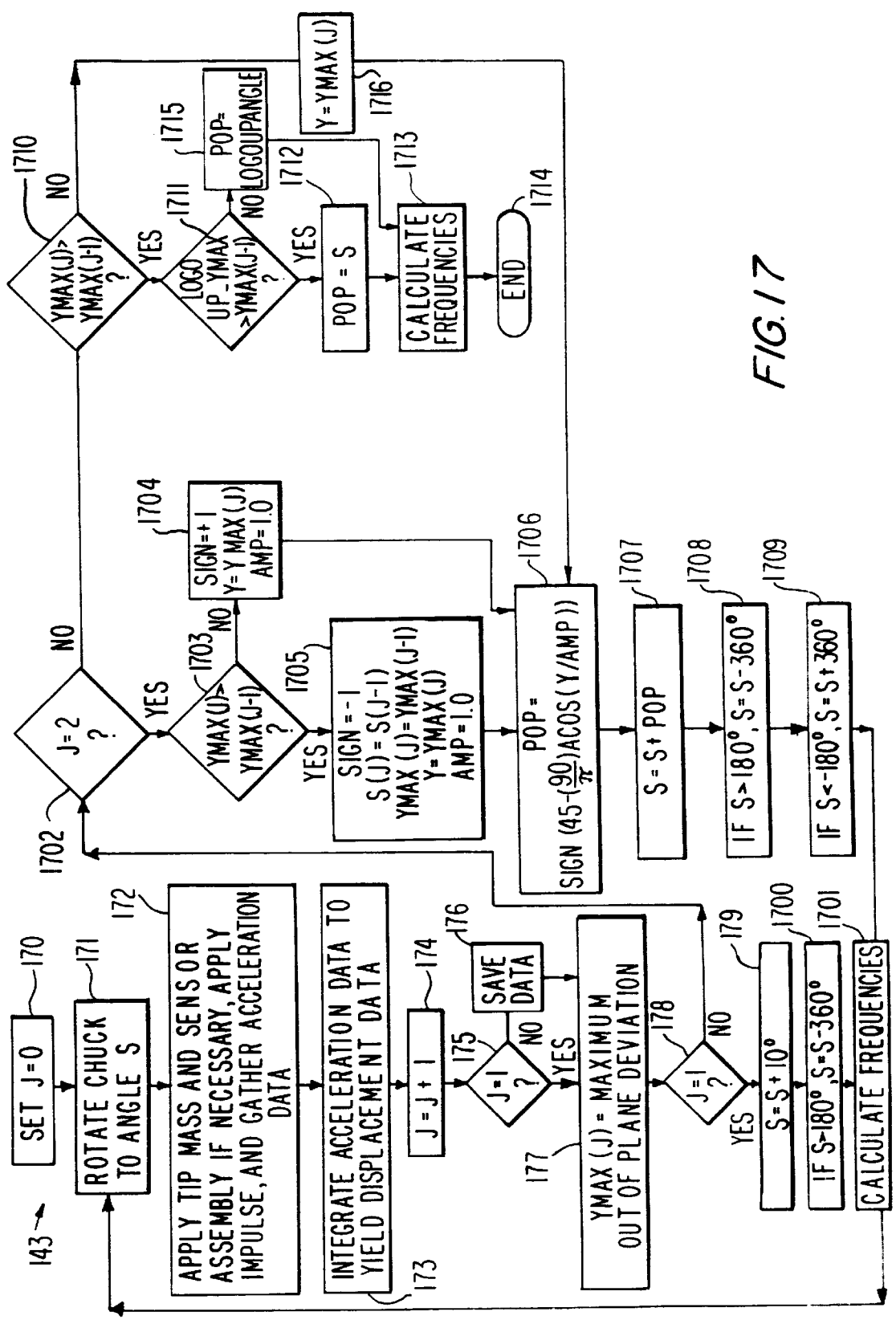
FIG. 17 is a flow diagram of a planar oscillation plane locating test performed according to the invention as part of the method of FIG. 14.

The system next proceeds to planar oscillation plane location test 143. As shown in FIG. 17, test 143 starts at step 170 where a counter J is initialized to zero. Next, at step 171, chuck 76, still holding shaft 110, is rotated to the start angle S previously computed. If no start angle S has been computed, test 143 starts at an arbitrary angle.

At step 172, if tip mass and sensor assembly 77 has not previously been attached to tip 112 it is attached, and in any case an impulse is applied to tip mass and sensor assembly 77 in one of the ways described above and orthogonal—preferably, horizontal and vertical—acceleration data are gathered, preferably for about 4 seconds. These data preferably are integrated at step 173 to yield orthogonal—preferably horizontal and vertical—displacement data as functions of time. At step 174, the counter J is incremented by one. At test 175, the system tests to see if J=1. If, as on this first pass, J=1, then the system skips directly to step 177.

At step 177, the system sets a variable YMAX(J) equal to the maximum out of plane deviation value from step 173. The system then proceeds to test 178 where it determines if J=1, meaning it is the first pass through the loop. There preferably are always at least three passes through the loop. If at test 178 J=1, then at step 179 the angle S is incremented by 100. At step 1700, in order to keep S between +180° and −180°, if S>180°, then S is set to S−360°. Next, at step 1701, the frequencies of the horizontal and vertical oscillations are determined; this may be done from the displacement-vs.-time data from step 173. Frequency data are commonly used to measure the stiffness of golf club shafts, and these data are useful for comparison.

After step 1701, the system loops back to step 172, and steps 172–174 are carried out again. This time, at test 175 J≠1, and at step 176 the data from step 173 are saved along with angle S, and the system proceeds to step 177. Again at step 177 variable YMAX(J) is set equal to the maximum out of plane deviation value from step 173. This time at test 178 J≠1, and the system proceed to test 1702 to determine if J=2. On this second pass, J=2 and the system proceeds to test 1703 to determine if YMAX(J)>YMAX(J−1). If not, that means in this iteration the out-of-plane excursions are smaller, meaning the angle S is closer to the preferred orientation—i.e., to the planar oscillation plane—and at step 1704 the variable SIGN is set to +1, the variable Y is set to the value of YMAX(J), and the variable AMP is set to 1.0, and the system proceeds to step 1706. If at test 1703 YMAX(J)>YMAX(J−1), that means in this iteration the out-of-plane excursions are larger, meaning the angle S is further from the planar oscillation plane, and at step 1705 the variable SIGN is set to −1, the variable S(J) is set to the value of S(J−1), the variable YMAX(J) is set to the value of the variable YMAX(J−1) and the variable Y is then set to the value of YMAX(J), and the variable AMP is again set to 1.0, and the system proceeds to step 1706. Note that in either step 1704 or step 1705, AMP can be set to a higher value to cause the result to converge sooner, but with lower accuracy, while setting AMP lower increases accuracy but increases the number of iterations before convergence. This is a trade-off between speed and accuracy.

At step 1706 the system calculates the variable POP= SIGN(45−(90/π)cos$^{-1}$(Y/AMP)), and at step 1707 the value of S is set to S+POP. At step 1708, in order to keep S between +180° and −180°, if S>180°, then S is set to S−360°. Similarly, at step 1709, in order to keep S between +180° and −180°, if S<−180°, then S is set to S+360°. The system then returns to step 1701 to calculate the frequencies, and once again loops back to step 172. This time, on the third pass, at test 178 J≠1, and at test 1702 J≠2, and the system advances to test 1710 to determine if YMAX(J)>YMAX(J−1). If it is, then the values are converging, and the system proceeds to test 1711 to determine if the out-of-plane excursion on the last iteration (YMAX(J−1)) is less than the maximum out-of-plane excursion during the "logo up" test 142. If it is, then the current orientation is the preferred orientation, and at step 1712 the variable POP, representing the preferred orientation, is set to the value of the variable S, representing the current orientation. At step 1713, the shaft frequencies are again calculated as in step 1701, and test 143 ends at 1714.

If at test 1711, the out-of-plane excursion on the last iteration (YMAX(J−1)) is not less than the maximum out-of-plane excursion during the "logo up" test 142, then at step 1715, the variable POP, representing the preferred orientation, is set to the "logo up" angle. At step 1713, the shaft frequencies are again calculated as in step 1701, and test 143 ends at 1714.

If at test 1710, YMAX(J) ≯ YMAX(J−1), then the values have not converged, then at step, 1716, Y is set to the value of YMAX(J). The system then recalculates POP at step 1706 and from there goes through the loop at least one more time.

If optional "logo up" test 142 is not performed, then if test 1710 indicates convergence, test 1711 is not performed and the system proceeds directly from test 1710 to step 1712.

After completing planar oscillation plane location test 143, the system proceeds to report printing step 144 where the values of the following data preferably are printed (and determined if necessary): load as a function of angle (as determined in load test 141); load symmetry index (LSI), which is a measure of the variability in stiffness of the shaft (LSI=100(1−(($P_{max}$−$P_{min}$)/$P_{max}$)), where $P_{max}$ and $P_{min}$ are the maximum and minimum loads, respectively, measured in step 152); displacement plot at the "logo up" angle; displacement plot at the POP angle; displacement as a function of time at the "logo up" angle and the "hard" and "soft" POP angles (the latter two should be exactly 180° apart); the horizontal and vertical frequencies and the maximum out-of-plane excursions at the "logo up" and POP angles; and a frequency index equal to the ratio of the horizontal frequency at the POP angle to the horizontal frequency at the "logo up" angle, which is a comparative measure, in the form of a percentage improvement, of stiffness in the hit direction as between the original "logo up" configuration of the golf club and the spine-aligned configuration.

Next at step 145 the data are saved. In a full save, all data are saved. There preferably is also a "quick save" in which all the data printed in step 144 are saved except for the complete load-vs.-angle data and the complete displacement data at the "logo up" and POP angles. Following saving step 145, process 140 ends at 146.

The process and apparatus according to the present invention can be used as part of a larger process or apparatus for assembling golf clubs, to produce "spine-aligned" golf clubs. Thus, each golf club shaft 110, having been marked with a reference mark at a predetermined location relative to the location of the spine, preferred orientation, or planar oscillation plane (whether or not marked to indicate the "hard" side), can be passed to a golf club assembly station where the marking on the shaft is identified and used to assemble a golf club with the spine or planar oscillation plane preferably substantially perpendicular to the golf club face. Depending on the relative speeds of planar oscillation plane locating apparatus 60 as compared to the golf club assembly station, more or fewer planar oscillation plane locating stations or assembly stations, as may be appropriate, can be provided. Thus, several planar oscillation plane location stations 60 may be used to feed a single golf club assembly station. A hopper may be provided at the golf club assembly station to act as a buffer in case the assembly station slows down or stops, or is not ready to accept a new golf club shaft 110 the moment the shaft arrives.

The golf club assembly station preferably is equipped with a scanner for identifying the mark made on golf club shaft 110 indicating the location of the planar oscillation plane. Once that mark has been identified, shaft 110 is rotated so that the mark is in a predetermined orientation for the type of golf club head to be attached to shaft 110, and that golf club head is held in a predetermined orientation as shaft 110 is assembled to the golf club head.

Alternatively, each golf club head could be provided with an alignment marking to which the marking on golf club shaft 110 must be matched. A scanner scans for the alignment marks on both shaft 110 and the golf club head and rotates shaft 110 until the two markings are aligned. This eliminates the need for the golf club head holding mechanism to "know" a specific orientation in which to hold each different type of golf club head for alignment with the marked shaft. Instead, each golf club head can be held in the same orientation, and as shaft 110 is brought close for assembly, shaft 110 can be rotated until the marking on shaft 110 and the marking on the golf club head are aligned before shaft 110 is joined to the golf club head.

Figure 18:
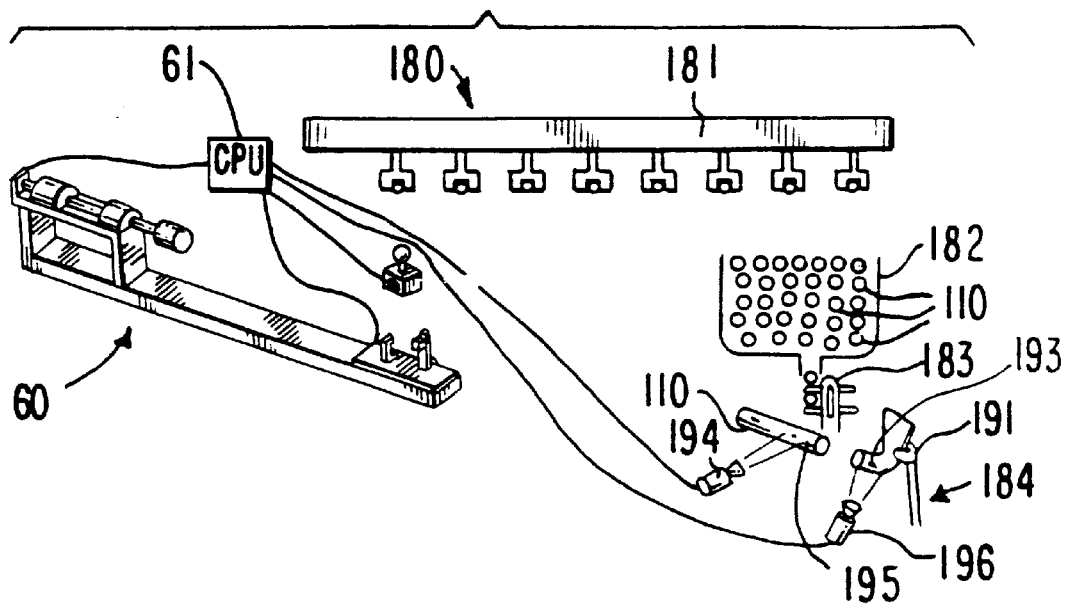
FIG. 18 is a diagrammatic view of apparatus according to the invention for assembling golf clubs.
Figure 19:
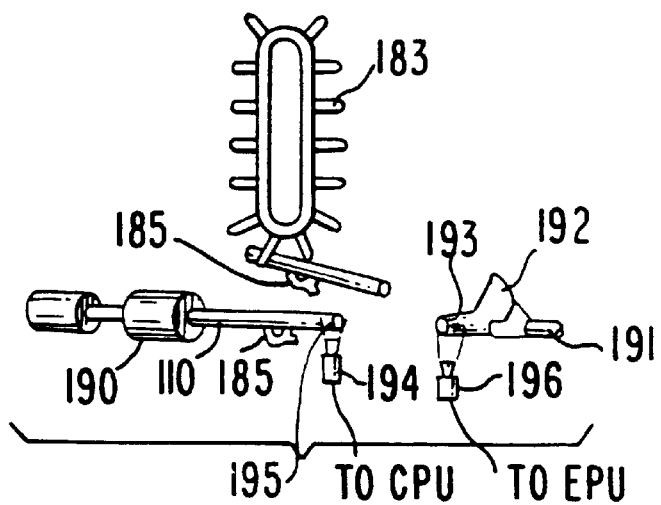
FIG. 19 is a close-up view of an assembly station of the apparatus of FIG. 18.

Apparatus 180 for assembling golf clubs in accordance with the present invention is shown in FIGS. 18 and 19. Apparatus 180 includes at least one apparatus 60 (one shown), a conveyor 181 for removing completed shafts 110 from apparatus 60 and depositing them in a hopper 182, a feed mechanism 183 for feeding each shaft 110 from hopper 182 to assembly station 184, and assembly station 184 itself.

At assembly station 184, feeder 183 including arms 185 connected to a motor (not shown) delivers shaft 110 to chuck 190, similar to chuck 76, which rotatably holds shaft 110 from its proximal end. Gripper 191 holds a golf club head 192, which may or may not bear an alignment marking 193; if there is no alignment marking 193, golf club head 192 is held by gripper 191 in a known position, which may differ for different types of golf club heads. A scanner 194 scans shaft 110 for marking 195 as chuck 190 rotates. When scanner 194 identifies marking 195, processor 61 instructs chuck 190 to align marking 195 with alignment marking 193 located by scanner 196, or with a predetermined orientation for golf club head 192. Chuck 190 and gripper 191 are then moved together by moving one or both thereof, and shaft 110 is joined to golf club head 192 in an otherwise conventional way, using whatever adhesives, ferrules, etc. as may be necessary.

Thus it is seen that a method and apparatus for quickly and reliably determining the preferred angular orientation of a golf club shaft, and for using the determination of the preferred angular orientation to automatically assemble golf clubs with each respective golf club shaft consistently aligned relative to the respective club face, are provided. One skilled in the art will appreciate that the present invention can be practiced by other than the described embodiments, which are presented for purposes of illustration and not of limitation, and the present invention is limited only by the claims which follow.

What is claimed is:

1. A method of determining a preferred angular orientation of a golf club shaft about a longitudinal axis thereof, said golf club shaft having a proximal end for gripping by a golfer and a distal end for attachment to a golf club head, said method comprising:

immobilizing a first one of said proximal end and said distal end of said golf club shaft;

initiating vibratory motion of a second one of said proximal end and said distal end of said golf club shaft in a direction other than parallel to said longitudinal axis;

analyzing said vibratory motion; and mathematically calculating from said analyzed vibratory motion said preferred angular orientation.

2. The method of claim 1 wherein:

said first one of said proximal end and said distal end of said golf club shaft is said proximal end; and said second one of said proximal end and said distal end of said golf club shaft is said distal end.

3. The method of claim 1 further comprising mounting a reaction mass on said distal end prior to said initiating.

4. The method of claim 3 wherein said initiating comprises applying an impulse to said golf club shaft in a direction other than parallel to said longitudinal axis.

5. The method of claim 4 wherein said applying an impulse comprises:
displacing said distal end of said golf club shaft in a direction other than parallel to said longitudinal axis; and
releasing said displaced distal end.

6. The method of claim 1 wherein said initiating comprises applying an impulse to said golf club shaft in a direction other than parallel to said longitudinal axis.

7. The method of claim 6 wherein said applying an impulse comprises:
displacing said distal end of said golf club shaft in a direction other than parallel to said longitudinal axis; and
releasing said displaced distal end.

8. The method of claim 1 wherein said analyzing comprises measuring displacement over time of said distal end in at least two directions other than parallel to said longitudinal axis.

9. The method of claim 8 wherein said two directions are perpendicular to each other and to said longitudinal axis.

10. The method of claim 8 wherein said calculating comprises calculating based on said displacement measured over time.

11. The method of claim 1 further comprising:
deimmobilizing said proximal end;
rotating said shaft through an angular displacement about said longitudinal axis;
reimmobilizing said proximal end; and
initiating subsequent vibratory motion of said distal end of said golf club shaft in a direction other than parallel to said longitudinal axis; wherein:
said analyzing and said calculating are based also on said subsequent vibratory motion.

12. The method of claim 11 further comprising iterating said deimmobilizing, said rotating, said reimmobilizing and said initiating, wherein said analyzing and said calculating are based also on each said subsequent vibratory motion, until said calculating converges on said preferred angular orientation.

13. The method of claim 1 further comprising marking a visible indicium on said golf club shaft to indicate said preferred angular orientation.

14. The method of claim 1 further comprising locating a hard side orientation by:
displacing said distal end, in a direction other than parallel to said longitudinal axis, to a displaced condition;
rotating said proximal end through at least about 360° of angular displacement while maintaining said distal end in said displaced condition;
measuring force tending to restore said distal end from said displaced condition during said rotating, and associating measured force with angular displacement; and
identifying as said hard side orientation an angular displacement associated with maximum measure force.

15. The method of claim 14 wherein said locating is performed after said calculating.

16. The method of claim 14 wherein said locating is performed prior to said initiating.

17. The method of claim 16 wherein said direction of said initiating of said vibratory motion is said hard side orientation.

18. A method of method of measuring asymmetry of a golf club shaft about a longitudinal axis thereof, said golf club shaft having a proximal end for gripping by a golfer and a distal end for attachment to a golf club head, said method comprising:
determining a preferred angular orientation of a golf club shaft about said longitudinal axis thereof by:
immobilizing a first one of said proximal end and said distal end of said golf club shaft,
initiating vibratory motion of a second one of said proximal end and said distal end of said golf club shaft in a direction other than parallel to said longitudinal axis,
analyzing said vibratory motion, and
calculating from said analyzed vibratory motion said preferred angular orientation;
making a predetermined orientation frequency measurement by:
aligning said immobilized golf club shaft so that a predetermined angular orientation is in a preselected angular position relative to said longitudinal axis,
initiating a predetermined orientation vibratory motion of said second one of said proximal end and said distal end in a direction other than parallel to said longitudinal axis while said predetermined angular orientation is in said preselected angular position relative to said longitudinal axis, and
measuring frequency of said predetermined orientation vibratory motion in a selected direction;
making a preferred orientation frequency measurement by:
aligning said immobilized golf club shaft so that said preferred angular orientation is in said preselected angular position relative to said longitudinal axis,
initiating a preferred orientation vibratory motion of said second one of said proximal end and said distal end in a direction other than parallel to said longitudinal axis while said preferred angular orientation is in said preselected angular position relative to said longitudinal axis, and
measuring frequency of said preferred orientation vibratory motion in said selected direction; and
calculating a frequency index as a ratio of said preferred orientation frequency measurement to said predetermined orientation frequency measurement.

19. The method of claim 18 wherein said making a preferred orientation frequency measurement occurs after said making a predetermined orientation frequency measurement.

20. The method of claim 18 wherein said making a preferred orientation frequency measurement occurs prior to said making a predetermined orientation frequency measurement.

21. The method of claim 18 wherein said preselected angular position is substantially vertical.

22. The method of claim 18 wherein said selected direction is substantially horizontal.

23. The method of claim 18 wherein said predetermined angular orientation is determined by a manufacturer logo on said golf club shaft.

24. A method of determining a preferred angular orientation of a golf club shaft about a longitudinal axis thereof, said golf club shaft having a proximal end for gripping by a golfer and a distal end for attachment to a golf club head, said method comprising:

locating a hard side orientation by:
        immobilizing a first one of said proximal end and said distal end of said golf club shaft,
        displacing a second one of said proximal end and said distal end, in a direction other than parallel to said longitudinal axis, to a displaced condition,
        rotating said immobilized end through at least about 360° of angular displacement while maintaining said displaced end in said displaced condition,
        measuring force tending to restore said displaced end from said displaced condition during said rotating, and associating measured force with angular displacement, and
        identifying as said hard side orientation an angular displacement associated with maximum measure force;
    immobilizing a first one of said proximal end and said distal end of said golf club shaft;
    initiating vibratory motion of a second one of said proximal end and said distal end of said golf club shaft in a direction other than parallel to said longitudinal axis;
    analyzing said vibratory motion; and
    calculating from said analyzed vibratory motion said preferred angular orientation.

25. A method of measuring asymmetry of a golf club shaft about a longitudinal axis thereof, said golf club shaft having a proximal end for gripping by a golfer and a distal end for attachment to a golf club head, said method comprising:

immobilizing a first one of said proximal end and said distal end of said golf club shaft;
    displacing a second one of said proximal end and said distal end, in a direction other than parallel to said longitudinal axis, to a displaced condition;
    rotating said immobilized end through at least about 360° of angular displacement while maintaining said displaced end in said displaced condition;
    measuring force tending to restore said displaced end from said displaced condition during said rotating, and associating values of measured force with respective angular displacements; and
    calculating, based on a formula involving said values of measured force at at least two of said angular displacements, an index, said index being a single indicium representative of said asymmetry of said shaft over all angles.

26. The method of claim 25 wherein said calculating comprises:

selecting, from said measured force associated with angular displacement, a maximum force $P_{max}$ and a minimum force $P_{min}$; and
    computing said index, LSI, according to the following equation:

$$LSI = 100(1-((P_{max}-P_{min})/P_{max})).$$

* * * * *